United States Patent
Allan et al.

(10) Patent No.: US 12,161,089 B2
(45) Date of Patent: Dec. 10, 2024

(54) PARASITICIDAL COLLAR COMPRISING ISOXAZOLINE COMPOUNDS

(71) Applicants: Boehringer Ingelheim Animal Health USA Inc., Duluth, GA (US); University of Georgia Research Foundation, Inc., Athens, GA (US)

(72) Inventors: James Allan, Suwanee, GA (US); Samuel David Bell, Cumming, GA (US); Christian Helmut Epe, Ingelheim (DE); Loic Patrick Le Hir De Fallois, Hopewell, NJ (US); Willy W. Lee, Piscataway, NJ (US); Jason J. Locklin, Bogart, GA (US)

(73) Assignees: Boehringer Ingelheim Animal Health USA Inc., Duluth, GA (US); University of Georgia Research Foundation, Inc., Athens, GA (US)

(*) Notice: Subject to any disclaimer, the term of this patent is extended or adjusted under 35 U.S.C. 154(b) by 123 days.

(21) Appl. No.: 17/457,792

(22) Filed: Dec. 6, 2021

(65) Prior Publication Data
US 2022/0201983 A1    Jun. 30, 2022

Related U.S. Application Data

(60) Provisional application No. 63/128,362, filed on Dec. 21, 2020.

(51) Int. Cl.
| | | |
|---|---|---|
| A01K 27/00 | (2006.01) | |
| A01N 43/80 | (2006.01) | |
| A61K 9/00 | (2006.01) | |
| A61K 31/422 | (2006.01) | |
| A61P 33/00 | (2006.01) | |
| C08L 27/06 | (2006.01) | |

(52) U.S. Cl.
CPC .......... *A01K 27/007* (2013.01); *A01K 27/001* (2013.01); *A01N 43/80* (2013.01); *A61K 9/0017* (2013.01); *A61K 31/422* (2013.01); *A61P 33/00* (2018.01); *C08L 27/06* (2013.01)

(58) Field of Classification Search
None
See application file for complete search history.

(56) References Cited

U.S. PATENT DOCUMENTS

| | | | |
|---|---|---|---|
| 3,852,416 A * | 12/1974 | Grubb | A01K 27/007 43/131 |
| 4,879,117 A | 11/1989 | Rombi | |
| 5,885,607 A | 3/1999 | Jeannin | |
| 6,413,532 B1 | 7/2002 | Focheux et al. | |
| 8,410,153 B2 | 4/2013 | Lahm et al. | |
| 8,598,087 B2 * | 12/2013 | Currie | A61P 33/10 548/240 |
| 2018/0221392 A1 * | 8/2018 | Chelle | A61K 47/34 |

FOREIGN PATENT DOCUMENTS

| | | |
|---|---|---|
| CN | 100398599 C | 7/2008 |
| CN | 109662958 A | 4/2019 |
| EP | 0542078 A1 | 5/1993 |
| EP | 2529628 B1 | 9/2016 |
| EP | 2391207 B1 | 3/2018 |
| WO | 0187065 A1 | 11/2001 |
| WO | 2008154528 A2 | 12/2008 |
| WO | 2009002809 A2 | 12/2008 |
| WO | 2009045999 A1 | 4/2009 |
| WO | 2010086102 A1 | 8/2010 |
| WO | 2011149749 A1 | 12/2011 |
| WO | 2012109715 A1 | 8/2012 |
| WO | 2018197466 A1 | 11/2018 |
| WO | 2019115492 A1 | 6/2019 |
| WO | 2020/201440 A1 | 10/2020 |
| WO | WO-2021005606 A1 * | 1/2021 ........... A01K 27/007 |

\* cited by examiner

*Primary Examiner* — Bethany P Barham
*Assistant Examiner* — Peter Anthopolos
(74) *Attorney, Agent, or Firm* — PABST PATENT GROUP LLP

(57) ABSTRACT

Provided herein are long-acting antiparasitic devices comprising parasiticidal isoxazoline active agent for external use on an animal to treat and/or prevent parasitic infestations by ectoparasites, and in some embodiments, also parasitic infections. The disclosure also describes methods and uses of the antiparasitic external devices to treat and/or prevent parasitic infestations and/or infections in an animal.

8 Claims, 9 Drawing Sheets

PARASITICIDAL COLLAR COMPRISING ISOXAZOLINE COMPOUNDS

CROSS REFERENCE TO RELATED APPLICATIONS

This application claims the benefit of U.S. Provisional Application No. 63/128,362, filed Dec. 21, 2020, which is incorporated herein by reference, in its entirety.

FIELD OF THE PRESENT DISCLOSURE

The present disclosure relates to an external antiparasitic device comprising an antiparasitic isoxazoline active agent. In one embodiment, the disclosure relates to an antiparasitic collar for pets, in particular cats and dogs. The antiparasitic collar of the invention is active against the ectoparasites of these animals, in particular fleas and ticks. The present disclosure also relates to the use of isoxazoline compounds for the manufacture of such collars or external devices, as well as to a treatment method relating thereto.

BACKGROUND OF THE PRESENT DISCLOSURE

Animals such as mammals and birds are often susceptible to parasite infestations/infections. These parasites may be ectoparasites, such as fleas,ticks and parasitic flies, and endoparasites such as nematodes and other worms. Domesticated animals, such as cats and dogs, are often infested with one or more of the following ectoparasites:

fleas (e.g. *Ctenocephalides* spp., such as *Ctenocephalides fells* and the like);
ticks (e.g. *Rhipicephalus* spp., *Ixodes* spp., *Dermacentor* spp., *Amblyomma* spp., and the like);
mites (e.g. *Demodex* spp., *Sarcoptes* spp., *Otodectes* spp., and the like);
lice (e.g. *Trichodectes* spp., *Cheyletiella* spp., *Linognathus* spp. and the like);
mosquitoes (*Aedes* spp., *Culex* spp., *Anopheles* spp. and the like); and
flies (*Haematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borreliosis (Lyme disease caused by *Borrelia burgdorferi*), babesiosis (or piroplasmosis caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, cattle and other bovines are affected by a large number of parasites. A parasite which is prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Animals and humans also suffer from endoparasitic infections including, for example, helminthiasis which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting companion animals and poultry. Other parasites which occur in the gastrointestinal tract of animals and humans include those from the genus *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*.

Certain isoxazoline compounds have been demonstrated to be effective against parasites that harm animals. For example, U.S. Pat. No. 7,964,204 (to DuPont, incorporated by reference herein in its entirety) discloses isoxazoline compounds according to formula (I) below, which are active against ectoparasites and/or endoparasites.

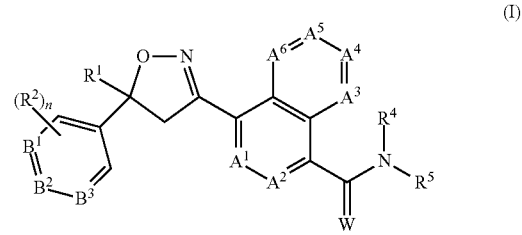

(I)

In addition, published patent application nos. US 2010/0254960 A1, WO 2007/070606 A2, WO 2007/123855 A2, WO 2010/003923 A1, US 2010/0137372 A1, US 2010/0179194 A2, US 2011/0086886 A2, US 2011/0059988 A1, US 2010/0179195 A1 and WO 2007/075459 A2 and U.S. Pat. Nos. 7,951,828 and 7,662,972 (all incorporated herein by reference) describe various other parasiticidal isoxazoline compounds. Other published patent applications that describe various other parasiticidal isoxazoline compounds and compositions comprising the same include WO 2007/079162 A1, WO 2008/154528 A1, WO 2009/002809 A2, WO 2011/149749 A1, WO 2014/439475 A1, U.S. Pat. No. 8,466,115, WO 2012/120399 A1, WO 2014/039484 A1, WO 2014/189837A1 (Zoetis), and WO2012/120135 A1 (Novartis). WO 2012/089623 A1 describes topical localized isoxazoline compositions comprising glycofurol. WO 2013/039948 A1 provides for topical veterinary compositions comprising at least one isoxazoline active agent and WO 2013/119442 A1 provides for oral veterinary compositions such as a soft chew which comprising at least one isoxazoline active agent. In additional to topical and oral dosage forms, solid antiparasitic external devices for external use, wherein the devices comprise a matrix, usually a biological acceptable polymer matrix which incorporates an effective amount of an active substance and is capable of releasing it over time, may be used. Isoxazoline compounds are believed to exhibit poor or weak insecticidal activity via contact exposure. Existing products containing isoxazoline active agents for cats and dogs are in the form of oral dosage forms or transdermal spot-on solutions (e.g. NexGard® (afoxolaner) chewables for dogs, Bravecto® (fluralaner) chews, Bravecto® (fluralaner) topical solution), Simparica™ (sarolaner) chewables, and Credilio™ (lotilaner) chewable tablets). For example, see Williams et al. "*Fluralaner activity against life stages of ticks using Rhipicephalus sanguineus and Ornithodoros moubat IN in vitro contact and feeding assays*," Parasites & vectors, 8(1), p. 90). Therefore, potent ectoparasiticidal efficacy from an external wearable device such as a parasiticidal collar containing an isoxazoline active agent would be unexpected.

Notwithstanding the highly active isoxazoline active agents and compositions comprising isoxazoline active agents alone or in combination with other active agents described in the documents above, there is a need for additional veterinary compositions and methods to provide more flexibility and longer duration of efficacy for pet owners to protect their pets against ectoparasites and possibly endoparasites. More specifically, there is a need to develop a long-acting external device composition comprising an isoxazoline compound which is effective against parasites (e.g., fleas and ticks) for a long duration (e.g., from three (3) to six (6) months or longer).

SUMMARY OF THE PRESENT DISCLOSURE

In a first aspect, the present disclosure provides for novel and inventive long-acting antiparasitic devices for external use such as an antiparasitic collar comprising an antiparasitic effective amount of at least one isoxazoline active agent for the treatment and/or prevention of parasite infections and/or infestations in an animal.

In a second aspect, the present disclosure provides for novel and inventive long-acting antiparasitic devices for external use such as an antiparasitic collar comprising an antiparasitic effective amount of tigolaner for the treatment of parasite infections and/or infestations in an animal. Tigolaner, which is listed in the BCPC Compendium of Pesticide Common Names (www.bcpc.org) has acaracidal and insecticidal activity and a similar mode of action to isoxazoline compounds. In one embodiment, the solid antiparasitic external devices according to the present disclosure contain effective amounts of tigolaner or tigolaner derivatives, salts, and analogues for the treatment and/or prevention of parasite infections and/or infestations in an animal.

The solid antiparasitic external devices according to the present disclosure are, for example, neck collars, pendants for neck collars (medallions), ear tags, collars for attachment to limbs or body parts. In some embodiments, the antiparasitic external device is a medallion, an ear tag and, in particular, a neck collar.

In some embodiments, the antiparasitic external devices according to the present disclosure comprises a polymer matrix containing one or more isoxazoline active agents, optionally in combination with other parasiticidal active agents and, where appropriate, additional auxiliary substances and additives. Accordingly, any additional auxiliary substances and additives included in the device are different substances than the polymers in the polymer matrix of the device.

The present disclosure further provides methods for the treatment and/or prevention of parasitic infestations, and in some embodiments, parasitic infections, in an animal comprising applying an antiparasitic external devices of the invention to the animal which allows the active ingredient(s) to be delivered to the animal in effective concentrations over a long duration. The provided methods allow for the delivery of effective concentrations of active ingredients (i.e. active agents) for an extended period.

In accordance with the first and second aspects of the present disclosure, the long-acting antiparasitic external device compositions of the invention comprising an isoxazoline active agent, or tigolaner or tigolaner derivatives, salts, and analogues (hereinafter a 'tigolaner compound'), show a long duration of efficacy. In addition, a single administration of the antiparasitic external device compositions of the invention generally provides potent activity against one or more parasites (e.g., ectoparasites), while also providing long duration of activity.

The present disclosure encompasses uses or veterinary uses of the antiparasitic external devices comprising an isoxazoline compound or tigolaner compound described herein for the treatment and/or prevention of parasitic infections and/or infestations in or on animals (either wild or domesticated), including livestock and companion animals such as cats, dogs, horses, chickens, sheep, goats, pigs, turkeys and cattle, with the aim of ridding these hosts of parasites commonly encountered by such animals.

The present disclosure also provides methods for administering an isoxazoline active agent or tigolaner compound to an animal by applying an antiparasitic external device comprising an effective amount of the isoxazoline active agent or tigolaner compound to the animal and thereby treating or preventing parasitic infections and/or infestations in the animal.

Surprisingly, it has been found that the isoxazoline-containing antiparasitic external device compositions described herein (e.g. antiparasitic collars) exhibit superior broad spectrum efficacy against harmful parasites (e.g. ectoparasites such as fleas and ticks) over a long duration compared to other compositions containing isoxazoline active agents known in the art or other known antiparasitic external device compositions.

This present disclosure also provides for the use of an isoxazoline active agent or a tigolaner compound in the preparation of a long-acting antiparasitic external device composition for the treatment and/or prevention of a parasitic infestation and/or infection in an animal.

In one embodiment, the present disclosure provides for a long-acting antiparasitic external device compositions comprising antiparasitic effective amounts of at least one isoxazoline of formula (I) shown below, or a pharmaceutically or veterinarily acceptable salt thereof, in combination and an acceptable polymer matrix, where variables $A^1$, $A^2$, $A^3$, $A^4$, $A^5$, $A^6$, $B^1$, $B^2$, $B^3$, $R^1$, $R^2$, $R^4$, $R^5$, W and n are defined herein.

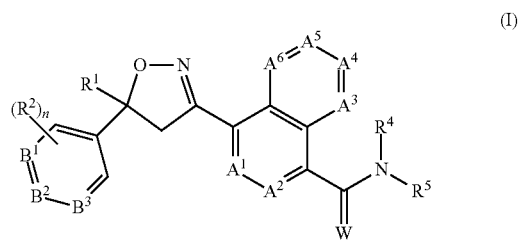

(I)

In another embodiment, the present invention provides a long-acting antiparasitic external device comprising a parasitic effective amount of an isoxazoline active agent of formula (Ia):

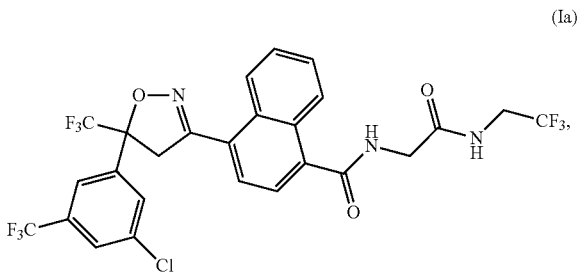 [SMILES: O=C(CNC(=O)c1ccc(C2=NOC(c3cc(Cl)cc(C(F)(F)F)c3)(C(F)(F)F)C2)c2ccccc12)NCC(F)(F)F]

(Ia)

or a pharmaceutically acceptable salt thereof, in combination with an acceptable polymer matrix. The compound of formula (Ia) is 4-[5-[3-chloro-5-(trifluoromethyl)phenyl]-4,5-dihydro-5-(trifluoromethyl)-3 soxazolyl]-N-[2-oxo-2-[(2,2,2-trifluoroethyl)amino]ethyl]-1-naphthalanecarboxamide (INN afoxolaner).

In another embodiment, the present disclosure provides a long-acting antiparasitic external device comprising an isoxazoline compound of formula (Ic):

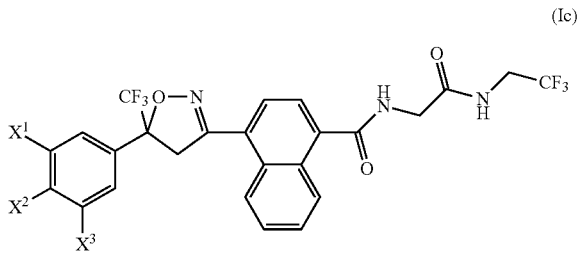

(Ic)

or a pharmaceutically acceptable salt thereof; wherein $X^1$, $X^2$ and $X^3$ are each independently H, halogen, $C_1$-$C_3$alkyl or $C_1$-$C_3$haloalkyl. In another embodiment, the invention provides an antiparasitic external device comprising a compound of formula (Ic) wherein $X^1$ is chloro, $X^2$ is fluoro and $X^3$ is $CF_3$ have been shown to have surprising excellent efficacy against external parasites.

In another embodiment, the present invention provides a long-acting solid antiparasitic external device composition comprising a parasitic effective amount of an isoxazoline active agent of formula (Id):

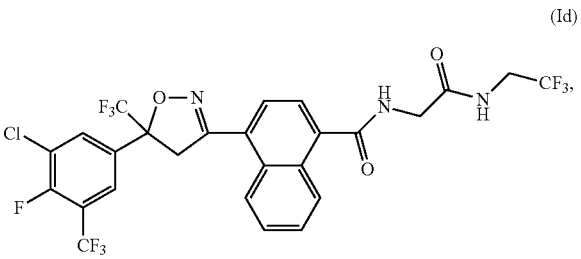 [SMILES: O=C(CNC(=O)c1ccc(C2=NOC(c3cc(Cl)c(F)c(C(F)(F)F)c3)(C(F)(F)F)C2)c2ccccc12)NCC(F)(F)F]

(Id)

or a pharmaceutically or veterinarily acceptable salt thereof, in combination with an acceptable polymer matrix.

In other embodiments, the invention provides long-acting antiparasitic external devices comprising a parasitic effective amount of an isoxazoline active agent of formula (Ib), (II), (III), (IV), (V), (Va), (VI) or (VIa) described herein, or pharmaceutically acceptable salts thereof, in combination with a suitable polymer matrix.

In other embodiments, the long-acting antiparasitic external device compositions of the invention may further comprise one or more additional active agents. In one embodiment, the long-acting antiparasitic external device compositions may comprise at least one macrocyclic lactone active agent, including, but not limited to, avermectins or milbemycins. In some embodiments, the avermectin or milbemycin active agent is eprinomectin, ivermectin, selamectin, milbemectin, milbemycin D, milbemycin oxime, or moxidectin.

The isoxazoline compounds used in the long-acting antiparasitic external device compositions of the invention are highly active against arthropod pests and parasites and useful for protecting animals, including livestock and companion animals such as cats, dogs, horses, chickens, sheep, goats, pigs, turkeys and cattle, from parasites that infest or infect such animals.

It is an object of the present disclosure to not encompass within the present disclosure any previously known product, process of making the product, or method of using the product such that the Applicants reserve the right and hereby disclose a disclaimer of any previously known product, process, or method. It is further noted that the present disclosure does not intend to encompass within the scope of the present disclosure any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

DETAILED DESCRIPTION

Figure 1:
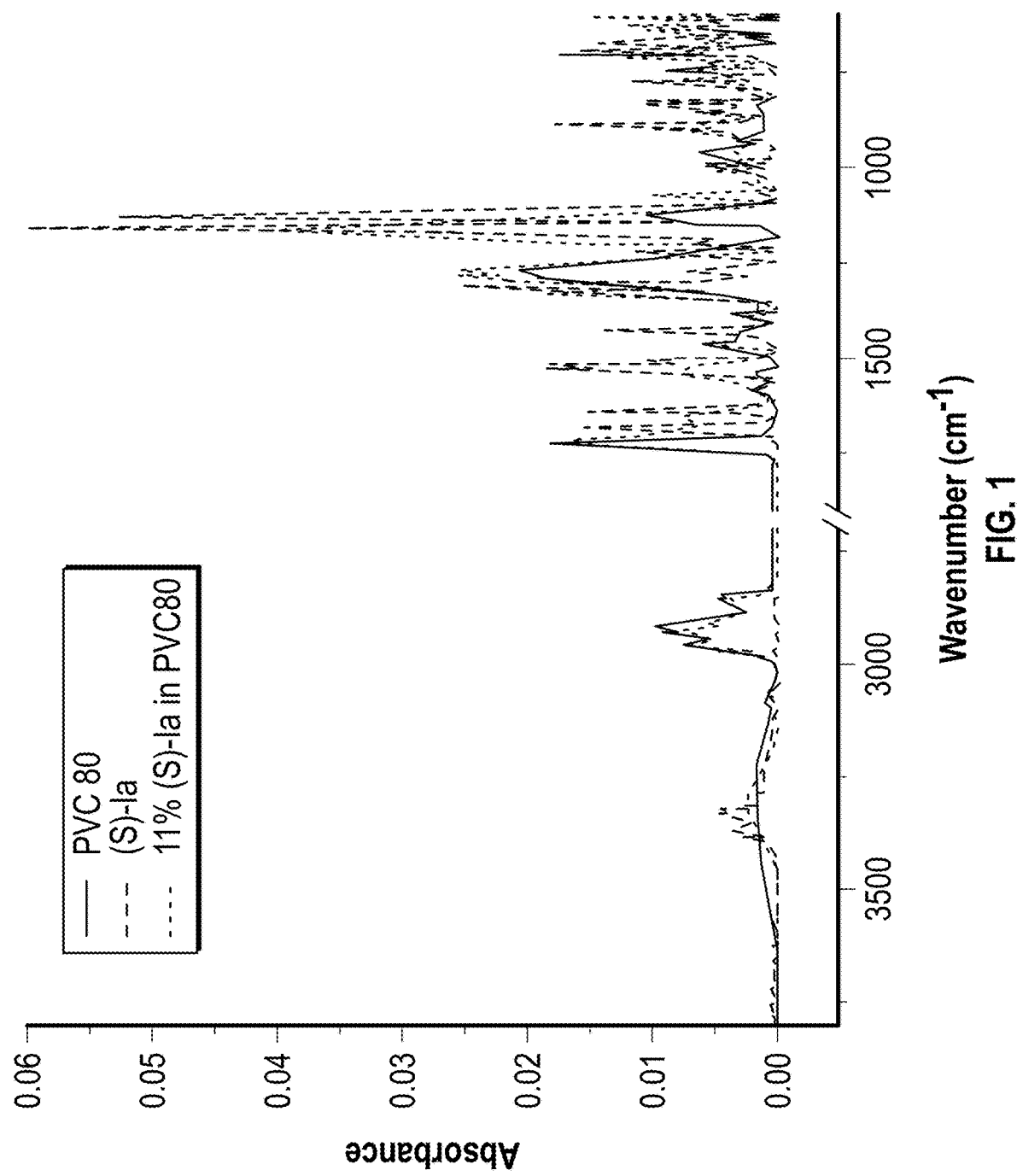
FIG. 1 ("Confirmation of (S)-Ia in PVC matrix after extrusion and processing.") shows overlaying Fourier-transform infrared spectroscopy ('FTIR') spectra of 1) a PVC80 matrix, 2) Compound (S)-Ia, and 3) a PVC80 matrix containing 11% (w/w) of compound (S)-Ia after extrusion and processing.

The present disclosure provides for long-acting antiparasitic external devices and device compositions for the treatment and/or prophylaxis of parasitic infections and infestations in or on animals comprising an antiparasitic effective amount of at least one isoxazoline compound and an acceptable polymer matrix.

In a first aspect, the present disclosure provides for novel and inventive long-acting antiparasitic external device compositions for the treatment or prevention of parasitic infections or infestations in an animal comprising an antiparasitic effective amount of at least one isoxazoline compound, one or more excipients and/or an acceptable polymer matrix, as defined herein are present.

In an embodiment, the present disclosure provides for novel and inventive long-acting antiparasitic external devices for the treatment or prevention of parasitic infections and/or infestations in an animal comprising an antiparasitic effective amount of at least one isoxazoline compound in combination with an antiparasitic effective amount of one or more additional active agents, one or more excipients and/or an acceptable polymer matrix, as defined herein are present.

Also provided are methods and uses for the treatment and/or prophylaxis of parasitic infections and/or infestations in or on animals, comprising administering to an animal in need thereof an antiparasitic external device comprising an antiparasitic effective amount of at least one isoxazoline compound, one or more excipients and an acceptable polymer matrix.

In another embodiment, the present disclosure provides for a long-acting an antiparasitic external device for the treatment and/or prophylaxis of parasitic infections and/or infestations in or on animals comprising:

a) an antiparasitic effective amount of at least one isoxazoline active agent, which is:
  i) an isoxazoline compound of formula (I):

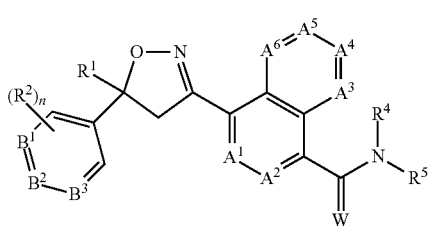

wherein:
$A_1$, $A_2$, $A_3$, $A_4$, $A_5$ and $A_6$ are independently selected from the group consisting of $CR^3$ and N, provided that at most 3 of $A^1$, $A^2$, $A^3$, $A^4$, $A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN, —$SF_5$ or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$SF_5$ or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$SF_5$, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1, 2 or 3; or a pharmaceutically acceptable salt thereof; and/or ii) an isoxazoline compound of formula (II):

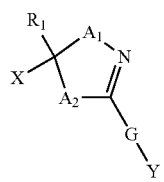

(II)

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

$A_1$ is oxygen; and
$A_2$ is oxygen, NR$_2$ or CR$_7$R$_8$;
G is G-1 or G-2;

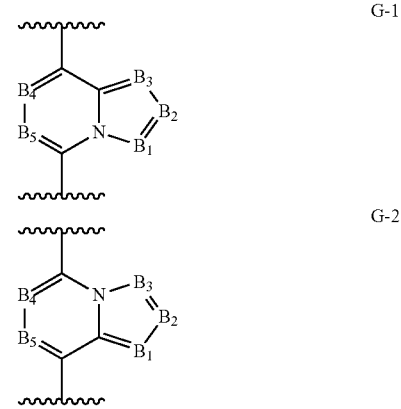

$B_1$, $B_2$, $B_3$, $B_4$ and $B_5$ are independently N or C—R$_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13;

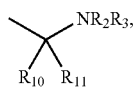

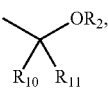

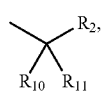

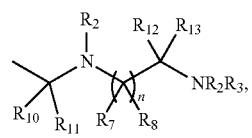

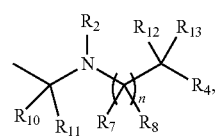

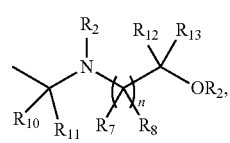

-continued

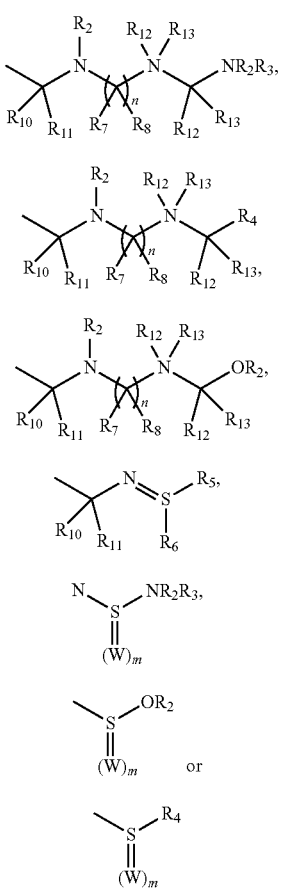

Y-7

Y-8

Y-9

Y-10

Y-11

Y-12

Y-13

$R_2$, $R_3$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, $R_{10}S(O)-$, $R_{10}S(O)_2-$, $R_{10}C(O)-$, $R_{10}C(S)-$, $R_{10}R^{11}NC(O)-$, $R_{10}R_{11}NC(S)-$ $R_{10}OC(O)-$;

$R_4$, $R_5$ and $R_6$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxyalkyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R_7S(O)-$, $R_7S(O)_2-$, $R_7C(O)-$, $R_7R_8NC(O)-$, $R_7OC(O)-$, $R_7C(O)O-$, $R_7C(O)NR_8-$, —CN or —NO$_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxyalkyl, alkenyl, haloalkenyl, alkynyl or haloalkynyl; or $R_{10}$ together with $R_{11}$ form =O, =S or =NR$_2$; or $R_{12}$ together with $R_{13}$ form =O, =S or =NR$_2$;

W is O, S or NR$_2$;

n is 1-4; and m is 0, 1 or 2; or a pharmaceutically acceptable salt thereof; and/or iii) an isoxazoline compound of formula (III)

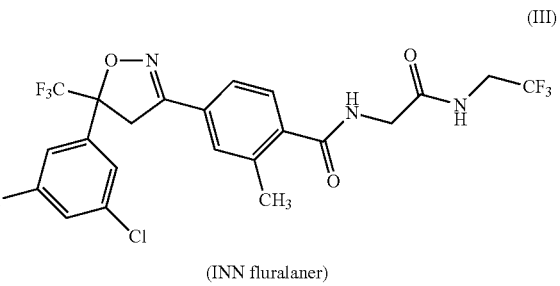

(III)

(INN fluralaner)

or a pharmaceutically acceptable salt thereof; and/or iv) an isoxazoline compound of formula (IV)

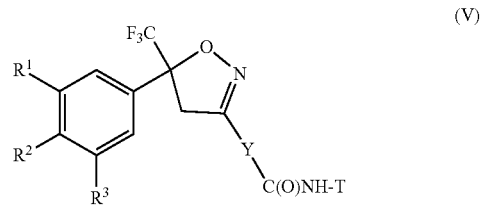

(IV)

or a pharmaceutically acceptable salt thereof; and/or v) an isoxazoline compound of formula (V):

(V)

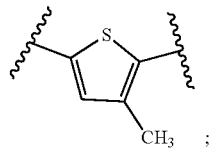

wherein $R^1$, $R^2$ and $R^3$ are independently H, Cl, F or CF$_3$;

Y is the diradical group and

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof; and/or vi) an isoxazoline compound of formula (VI):

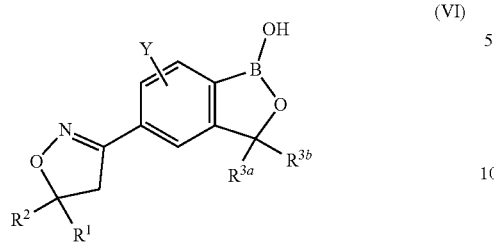

wherein Y is hydrogen, fluoro, chloro or bromo;
   $R^1$ is phenyl substituted with 2-4 substituents selected from halogen, methyl, difluoromethyl, trifluoromethyl, methoxy, trifluoromethoxy or trifluoroethoxy;
   $R^2$ is methyl, fluoromethyl, trifluoromethyl or perfluoroethyl;
   $R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
   a) an antiparasitic effective amount of an isoxazoline compound of formula (Ia)

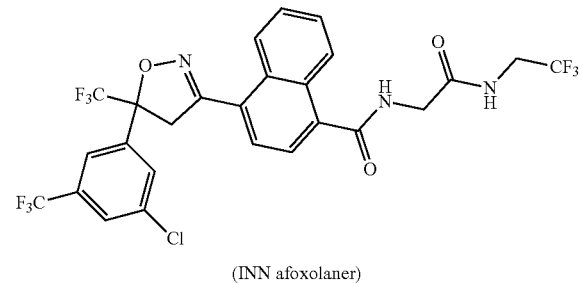

(INN afoxolaner)

or a pharmaceutically acceptable salt thereof;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
   a) an antiparasitic effective amount of an isoxazoline compound of formula (Ib)

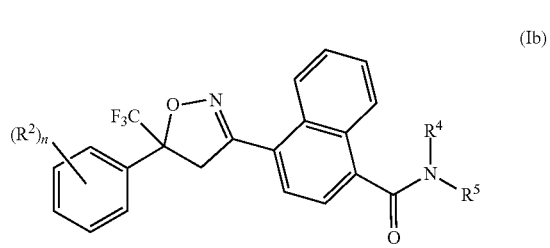

or a pharmaceutically acceptable salt thereof,
wherein
   $R^2$ independently is halogen, $C_1$-$C_6$ alkyl or $C_1$-$C_6$ haloalkyl
   $R^4$ is H or $C_1$-$C_6$ alkyl;
   $R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl (e.g., —$CH_2C(O)NHCH_2CF_3$); and n is 0, 1 or 2;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
   a) an antiparasitic effective amount of an isoxazoline compound of formula (Ic)

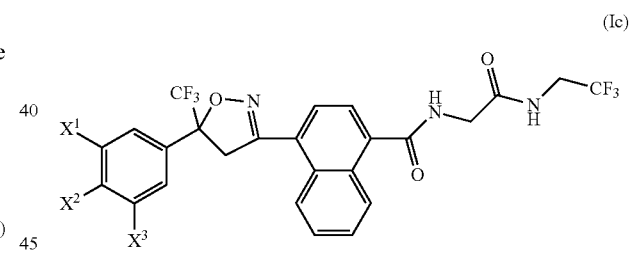

or a pharmaceutically acceptable salt thereof,
wherein
   $X^1$, $X^2$ and $X^3$ are each independently H, halogen, $C_1$-$C_3$ alkyl or $C_1$-$C_3$ haloalkyl;
b) an acceptable polymer matrix; and
c) optionally, at least one pharmaceutically acceptable additive, excipient or mixtures thereof.

In one embodiment, the long-acting antiparasitic external devices of the present disclosure comprise a compound of formula (Ic) wherein $X^1$ and $X^3$ are independently halogen and $X^2$ is hydrogen.

In another embodiment, the long-acting antiparasitic external devices of the present disclosure comprise a compound of formula (Ic), wherein $X^1$, $X^2$ and $X^3$ are each independently halogen.

In another embodiment of the present disclosure, the long-acting antiparasitic external devices comprise a compound of formula (Ic), wherein $X^1$ and $X^3$ are each independently halogen and $X^2$ is $C_1$-$C_3$haloalkyl.

In still another embodiment, the present disclosure provides a long-acting antiparasitic external device comprising a compound of formula (Ic), wherein $X^1$ and $X^2$ are independently halogen and $X^3$ is $C_1$-$C_3$haloalkyl.

In another embodiment, the present disclosure provides a long-acting antiparasitic external device comprising a compound of formula (Ic), wherein $X^1$ and $X^2$ are independently halogen and $X^3$ is $CF_3$.

In another embodiment, the present disclosure provides a long-acting antiparasitic external device comprising a compound of formula (Ic), wherein $X^1$ and $X^3$ are chloro and $X^2$ is hydrogen.

In yet another embodiment, the present disclosure provides a long-acting antiparasitic external device comprising a compound of formula (Ic), wherein $X^1$ is chloro, $X^2$ is fluoro and $X^3$ is $CF_3$.

In another embodiment, the present disclosure provides a long-acting antiparasitic external device comprising a compound of formula (Ic), wherein $X^1$ and $X^3$ are chloro and $X^2$ is fluoro.

In another embodiment, the present disclosure provides for a long-acting antiparasitic external device for the treatment and/or prevention (prophylaxis) of parasitic infections and/or infestations in or on animals comprising:
  a) an antiparasitic effective amount of an isoxazoline compound of formula (Ic)

(Ic)

or a pharmaceutically acceptable salt thereof,
wherein
$X^1$ and $X^3$ are each independently halogen or $C_1$-$C_3$ haloalkyl; and
$X^2$ is halogen or hydrogen;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and infestations in or on animals comprising:
  a) an antiparasitic effective amount of an isoxazoline compound of formula (Ic) as shown above,
  or a pharmaceutically acceptable salt thereof,
  wherein
  $X^1$ and $X^2$ are each independently chloro or fluoro; and
  $X^3$ is chloro or $CF_3$;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
  a) an antiparasitic effective amount of an isoxazoline compound of formula (Ic) as shown above, or a pharmaceutically acceptable salt thereof.

wherein
$X^1$ and $X^3$ are each chloro; and
$X^2$ is fluoro or hydrogen;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
  a) an antiparasitic effective amount of an isoxazoline compound of formula (Ic) as shown above,
  or a pharmaceutically acceptable salt thereof,
  wherein
  $X^1$ is chloro;
  $X^2$ is fluoro; and
  $X^3$ is $CF_3$;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
  a) an antiparasitic effective amount of an isoxazoline compound of formula (Ic) as shown above, or a pharmaceutically acceptable salt thereof,
  wherein
  $X^1$ and $X^3$ are chloro; and
  $X^2$ is fluoro;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
  a) an antiparasitic effective amount of an isoxazoline compound of formula (Ic) as shown above,
  or a pharmaceutically acceptable salt thereof,
  wherein
  $X^1$, $X^2$ and $X^3$ are each chloro;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
  a) an antiparasitic effective amount of an isoxazoline compound of formula (Ic) as shown above,
  or a pharmaceutically acceptable salt thereof,
  wherein
  $X^1$, $X^2$ and $X^3$ are each independently chloro or fluoro;
  b) an acceptable polymer matrix; and
  c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:

a) an antiparasitic effective amount of at least one isoxazoline compound of formula (Id)

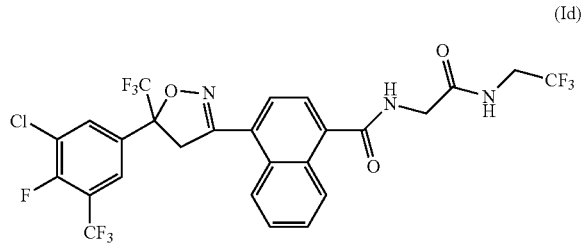 [SMILES: O=C(CNC(=O)c1ccc(C2=NOC(c3cc(Cl)c(F)c(C(F)(F)F)c3)(C(F)(F)F)C2)c2ccccc12)NCC(F)(F)F]

or a pharmaceutically acceptable salt thereof;

b) an acceptable polymer matrix; and c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:

a) an antiparasitic effective amount of at least one isoxazoline compound of formula (II) as described above, or a pharmaceutically acceptable salt thereof, b) an acceptable polymer matrix; and c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:

a) an antiparasitic effective amount of at least one isoxazoline compound of formulae II-1.001 to II-1.025 or II-2.001-II-2.018:

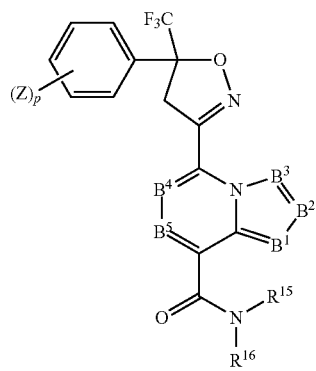

Compounds II-1.001 to II-1.025

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-Cl$_2$ | C—H | C—H | C—H | C—H | N | H | CH$_2$C(O)NHCH$_2$CF$_3$ |
| 1.002 | 3,5-Cl$_2$ | C—H | C—H | C—H | C—H | N | H | CH$_2$CF$_3$ |
| 1.003 | 3,5-(CF$_3$)$_2$ | C—H | C—H | C—H | C—H | N | CH$_3$ | CH$_2$CO$_2$CH$_3$ |
| 1.004 | 3,5-(CF$_3$)$_2$ | C—H | C—H | C—H | C—H | N | CH$_3$ | CH$_2$CO$_2$H |
| 1.005 | 3,5-(CF$_3$)$_2$ | C—H | C—H | C—H | C—H | N | CH$_3$ | CH$_2$C(O)NHCH$_2$CF$_3$ |
| 1.006 | 3,5-(CF$_3$)$_2$ | C—H | C—H | C—H | C—H | N | H | CH$_2$C(O)NHCH$_2$CF$_3$ |
| 1.007 | 3,5-(CF$_3$)$_2$ | C—H | C—H | C—H | C—H | N | H | CH$_2$CH$_2$SCH$_3$ |
| 1.008 | 3,5-(CF$_3$)$_2$ | C—H | C—H | C—H | C—H | C—H | H | CH$_2$C(O)NHCH$_2$CF$_3$ |
| 1.009 | 3,5-(CF$_3$)$_2$ | C—H | C—H | C—H | C—H | C—H | H | CH$_2$CH$_2$SCH$_3$ |
| 1.010 | 3,5-(CF$_3$)$_2$ | C—H | C—H | C—H | C—H | C—H | H | CH$_2$CF$_3$ |
| 1.011 | 3,5-Cl$_2$ | C—H | C—H | C—H | C—H | C—H | H | CH$_2$C(O)NHCH$_2$CF$_3$ |
| 1.012 | 3,5-Cl$_2$ | C—H | C—H | C—H | C—H | C—H | H | CH$_2$CF$_3$ |
| 1.013 | 3,5-Cl$_2$ | C—H | C—H | C—H | C—H | C—H | H | CH$_2$CH$_2$SCH$_3$ |
| 1.014 | 3-Cl,5-CF$_3$ | C—H | C—H | C—H | C—H | C—H | H | CH$_2$C(O)NHCH$_2$CF$_3$ |
| 1.015 | 3-Cl,5-CF$_3$ | C—H | C—H | C—H | C—H | C—H | H | CH$_2$CF$_3$ |
| 1.016 | 3-Cl,5-CF$_3$ | C—H | C—H | C—H | C—H | C—H | H | CH$_2$CH$_2$SCH$_3$ |
| 1.017 | 3,5-Cl$_2$ | C—H | C—H | C—Me | C—H | C—Me | H | CH$_2$C(O)NHCH$_2$CF$_3$ |
| 1.018 | 3,5-Cl$_2$ | C—H | C—H | C—Me | C—H | C—Me | H | CH$_2$CF$_3$ |
| 1.019 | 3,5-Cl$_2$ | C—H | C—H | C—Me | C—H | C—Me | H | CH$_2$CH$_2$SCH$_3$ |
| 1.020 | 3,5-(CF$_3$)$_2$ | C—H | C—H | C—Me | C—H | C—Me | H | CH$_2$C(O)NHCH$_2$CF$_3$ |
| 1.021 | 3,5-(CF$_3$)$_2$ | C—H | C—H | C—Me | C—H | C—Me | H | CH$_2$CF$_3$ |
| 1.022 | 3,5-(CF$_3$)$_2$ | C—H | C—H | C—Me | C—H | C—Me | H | CH$_2$CH$_2$SCH$_3$ |
| 1.023 | 3-Cl,5-CF$_3$ | C—H | C—H | C—Me | C—H | C—Me | H | CH$_2$C(O)NHCH$_2$CF$_3$ |
| 1.024 | 3-Cl,5-CF$_3$ | C—H | C—H | C—Me | C—H | C—Me | H | CH$_2$CF$_3$ |
| 1.025 | 3-Cl,5-CF$_3$ | C—H | C—H | C—Me | C—H | C—Me | H | CH$_2$CH$_2$SCH$_3$ |

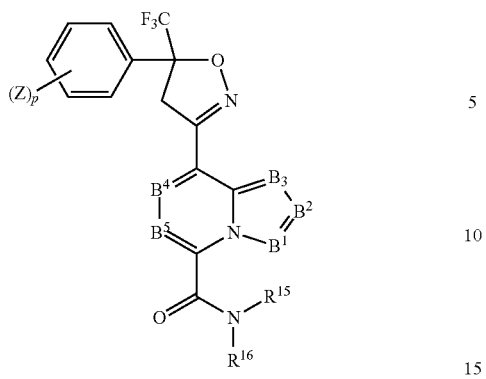

Compounds II-2.001 to II-2.018

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 2.001 | 3,5-Cl$_2$ | C—H | C—H | N | C—H | C—H | H | CH$_2$C(O)NHCH$_2$CF$_3$ |
| 2.002 | 3,5-Cl$_2$ | C—H | C—H | N | C—H | C—H | H | CH$_2$CF$_3$ |
| 2.003 | 3,5-Cl$_2$ | C—H | C—H | N | C—H | C—H | H | CH$_2$CH$_2$SCH$_3$ |
| 2.004 | 3,5-(CF$_3$)$_2$ | C—H | C—H | N | C—H | C—H | H | CH$_2$C(O)NHCH$_2$CF$_3$ |
| 2.005 | 3,5-(CF$_3$)$_2$ | C—H | C—H | N | C—H | C—H | H | CH$_2$CF$_3$ |
| 2.006 | 3,5-(CF$_3$)$_2$ | C—H | C—H | N | C—H | C—H | H | CH$_2$CH$_2$SCH$_3$ |
| 2.007 | 3-Cl,5-CF$_3$ | C—H | C—H | N | C—H | C—H | H | CH$_2$C(O)NHCH$_2$CF$_3$ |
| 2.008 | 3-Cl,5-CF$_3$ | C—H | C—H | N | C—H | C—H | H | CH$_2$CF$_3$ |
| 2.009 | 3-Cl,5-CF$_3$ | C—H | C—H | N | C—H | C—H | H | CH$_2$CH$_2$SCH$_3$ |
| 2.010 | 3,5-Cl$_2$ | C—H | C—H | C—H | C—H | C—H | H | CH$_2$C(O)NHCH$_2$CF$_3$ |
| 2.011 | 3,5-Cl$_2$ | C—H | C—H | C—H | C—H | C—H | H | CH$_2$CF$_3$ |
| 2.012 | 3,5-Cl$_2$ | C—H | C—H | C—H | C—H | C—H | H | CH$_2$CH$_2$SCH$_3$ |
| 2.013 | 3,5-(CF$_3$)$_2$ | C—H | C—H | C—H | C—H | C—H | H | CH$_2$C(O)NHCH$_2$CF$_3$ |
| 2.014 | 3,5-(CF$_3$)$_2$ | C—H | C—H | C—H | C—H | C—H | H | CH$_2$CF$_3$ |
| 2.015 | 3,5-(CF$_3$)$_2$ | C—H | C—H | C—H | C—H | C—H | H | CH$_2$CH$_2$SCH$_3$ |
| 2.016 | 3-Cl,5-CF$_3$ | C—H | C—H | C—H | C—H | C—H | H | CH$_2$C(O)NHCH$_2$CF$_3$ |
| 2.017 | 3-Cl,5-CF$_3$ | C—H | C—H | C—H | C—H | C—H | H | CH$_2$CF$_3$ |
| 2.018 | 3-Cl,5-CF$_3$ | C—H | C—H | C—H | C—H | C—H | H | CH$_2$CH$_2$SCH$_3$ | or a pharmaceutically acceptable salt thereof;

b) an acceptable polymer matrix; and c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:

a) an antiparasitic effective amount of at least one isoxazoline compound of formulae II-1.001 to II-1.025 or II-2.001-II-2.018 as described above, or a pharmaceutically acceptable salt thereof;

b) an acceptable polymer matrix; and c) optionally, a pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:

a) an antiparasitic effective amount of an isoxazoline compound of formula (III)

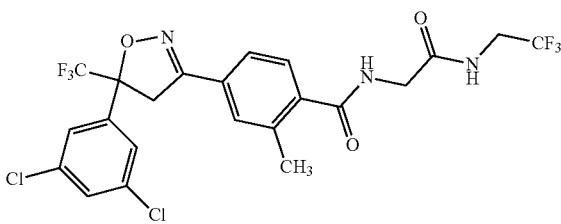

(III)

or a pharmaceutically acceptable salt thereof;

b) an acceptable polymer matrix; and c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:

a) an antiparasitic effective amount of an isoxazoline compound of formula (IV)

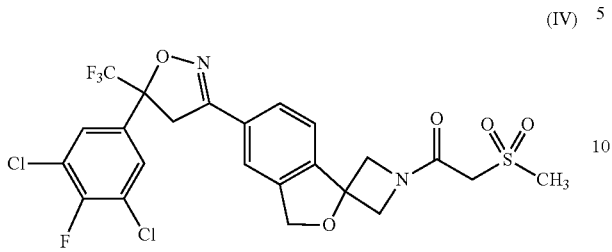

(IV)

or a pharmaceutically acceptable salt thereof;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
a) an antiparasitic effective amount of at least one isoxazoline compound of formula (V)

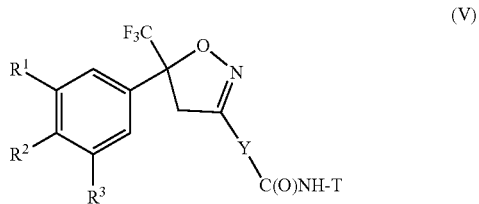

(V)

or a pharmaceutically acceptable salt thereof;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising
a) an antiparasitic effective amount of an isoxazoline compound of formula (Va)

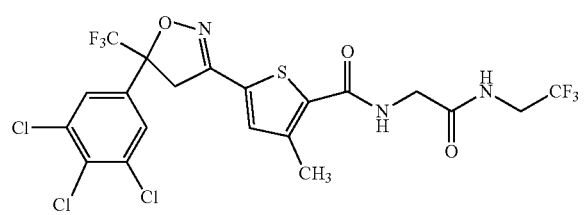

(Va)

or a pharmaceutically acceptable salt thereof;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising a) an antiparasitic effective amount of at least one compound of formula (VI)

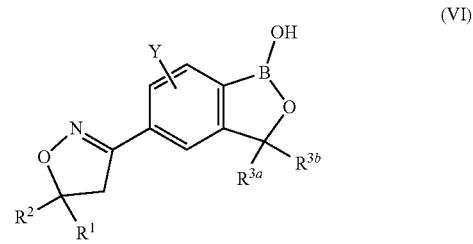

(VI)

or a pharmaceutically acceptable salt thereof;
b) an acceptable polymer matrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
a) an antiparasitic effective amount of at least one compound of formula (VIa)

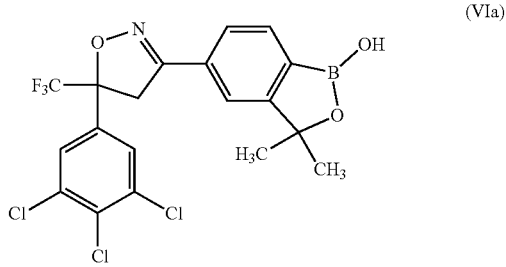 [SMILES: CC1(C)OB(O)c2ccc(C3=NOC(c4cc(Cl)c(Cl)c(Cl)c4)(C(F)(F)F)C3)cc21]

(VIa)

or a pharmaceutically acceptable salt thereof;
b) an acceptable polymermatrix; and
c) optionally, at least one pharmaceutically acceptable additive, excipient or mixtures thereof.

In another embodiment, the present disclosure provides for a long-acting antiparasitic external device for the treatment and/or prevention (prophylaxis) of parasitic infections and/or infestations in or on animals comprising:
a) an antiparasitic effective amount of at least one compound of formula (VII)

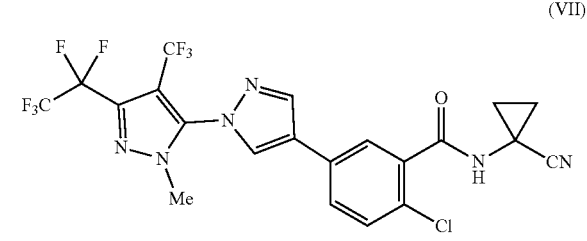

(VII)

(INN: tigolaner)

or a pharmaceutically acceptable salt thereof;
b) an acceptable polymer matrix; and
c) optionally, at least one pharmaceutically acceptable additive, excipient or mixtures thereof.

Stereoisomers

The compounds of formula (I) through formula (VIa) shown above can exist as stereoisomers, and each individual stereoisomer present is encompassed by the structural formulas depicted herein. Where compounds within the compositions of the present disclosure include n chiral centers, the compounds may comprise up to $2^n$ optical isomers. The present disclosure encompasses compositions comprising the specific enantiomers or diastereomers of each compound as well as mixtures of different enantiomers and/or diastereomers of the compounds of the present disclosure that possess the useful properties described herein. In addition, the present disclosure encompasses compositions comprising one or more conformational isomers (e.g. rotamers) as well as mixtures of conformational isomers. Conformational isomers of the isoxazoline compounds may be produced, for example, by a restriction of rotation about the amide bond bonded to the aryl or heteroaryl ring (e.g. the amide bonded to the naphthyl group in formula (I)). For avoidance of doubt, when an isoxazoline compound (e.g. any of the isoxazoline active agents as described herein) includes two or more stereoisomers (e.g. an (S)- and (R)-enantiomers), the formulae depicted herein that does not explicitly include stereochemical configurations encompasses each of the possible stereoisomers. One of skill in the art will understand that one stereoisomer of an active isoxazoline compound may be more active and/or may exhibit beneficial properties relative to the other enantiomer. In addition, the skilled person in the art knows how to separate, enrich, and/or selectively prepare a stereoisomer of the isoxazoline compounds described herein. The isoxazoline compounds described herein contain a chiral quaternary carbon atom in the five-membered isoxazoline ring (shown by the asterisk (*) in the structures below); therefore, the compounds will contain at least two possible stereoisomers. As an example for the compound of formula (Ia), the two possible stereoisomers resulting from the quaternary carbon are shown as formulae (S)-Ia and (R)-Ia:

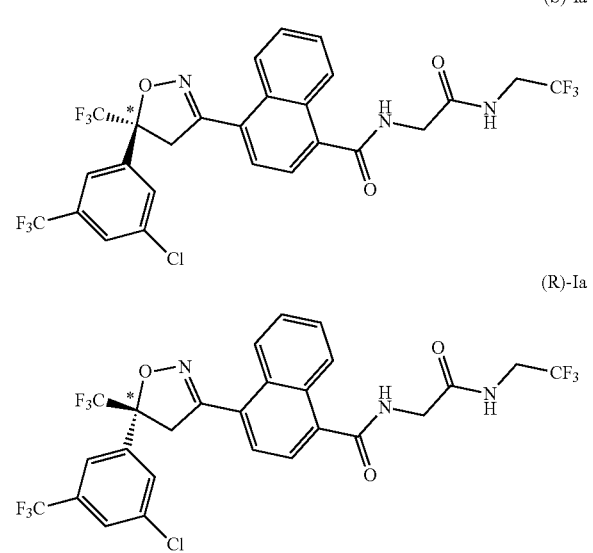

(S)-Ia (R)-Ia

The compound of formula (S)-Ia above has the (S) configuration at the chiral carbon atom and the compound of formula (R)-Ia has the (R) configuration. Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereo configuration is intended to be specified.

The optically active forms of the isoxazoline compounds can be prepared by methods known in the art, for example, by resolution of the racemic forms by selective crystallization techniques, by synthesis from optically active precursors, by chiral synthesis, by chromatographic separation using a chiral stationary phase or by enzymatic resolution.

It will be appreciated that in addition to the compounds of formula (Ia), the other isoxazoline compounds of formula (I), formula (Ib), formula (Ic), (Id), formula (II), formula (II-1.1001) to formula (II-1.025), formula (II-2.001) to formula (II-2.018), formula (III), formula (IV), formula (V), formula (Va), formula (VI) and formula (VIa) will also have at least two possible enantiomers as a result of the quaternary carbon atom on the isoxazoline ring. In addition, certain compounds may include other chiral centers in one or more substituents resulting in diastereomers.

In one embodiment of the present disclosure, the more biologically active enantiomer is believed to be formula (S)-Ia (which is and understanding based on previous investigations of the parasiticidal effectiveness of the enantiomers of the compound of formula (Ia) in other product types such as oral, injectable and spot-on compositions). In one embodiment of the present disclosure, the more biologically active enantiomer is formula (S)-Ia. Similarly, the more biologically active enantiomers of isoxazoline compounds of formula (Ib), (Ic), (Id) and (II) to (VIa) are believed to have the (S) configuration at the chiral carbon of the isoxazoline ring. In certain embodiments, an isoxazoline compound of the present disclosure, or compositions comprising the compound, are enriched in an enantiomer that displays significant in vitro and in vivo activity (the eutomer) with a favorable toxicity profile relative to a compound or a composition enriched with the other corresponding enantiomer that displays significantly less in vitro and in vivo activity (the distomer).

When enantiomerically enriched, one enantiomer is present in greater amounts than the other, and the extent of enrichment may be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers). In some embodiments, the compositions of the present disclosure comprise compounds that have at least a 50% enantiomeric excess. In other embodiments, the compositions of the present disclosure comprise compounds that have at least a 75% enantiomeric excess, at least a 90% enantiomeric excess, or at least a 94% enantiomeric excess of the more active isomer. Of particular note are enantiomerically pure embodiments of the more active isomer (the eutomer).

This present disclosure comprises racemic mixtures, for example, equal amounts of the enantiomers of the isoxazoline compounds of formulae (I) to (VIa). The present disclosure also includes compounds of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), that are enriched in one enantiomer compared to the racemic mixture. Also included are the essentially pure enantiomers of the compounds of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa).

Hence, in one embodiment, the long-acting antiparasitic external devices of present disclosure comprise an antiparasitic effective amount of at least one isoxazoline of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), which is substantially enriched in one enantiomer, or a pharmaceutically acceptable salt thereof. The term "substantially enriched" means that the compound is enriched in a weight:weight ratio of at least about 1.5 or higher in favor of the desired enantiomer. In another embodiment, the long-acting compositions of the present disclosure comprise at least one isoxazoline compound of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa) that are enriched in one enantiomer in a weight:weight ratio of at least 2:1, at least 5:1 or at least 10:1. In another embodiment, the compositions comprise at least one compound of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), which is enriched in one enantiomer in a weight:weight ratio of at least 15:1 or at least 20:1, or a pharmaceutically acceptable salt thereof. In an embodiment, the isoxazoline compounds of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa) present in the compositions of the present disclosure are essentially pure enantiomers.

In another embodiment of the present disclosure, the compositions comprise a compound of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), that is enriched in the (S)-enantiomer in a weight:weight ratio is at least approximately 1.5:1 or 2:1. In yet another embodiment, the compositions of the present disclosure comprise a compound of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), that is enriched in the (S)-enantiomer in a weight:weight ratio of at least about 5:1 or greater. In still another embodiment, the compositions of the present disclosure comprise a compound of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), that is enriched in the (S)-enantiomer in a weight:weight ratio of at least approximately 10:1, 20:1, or greater. In still another embodiment, the compositions of the present disclosure comprise a compound of formula (I), formula (Ia), formula (Ib), formula (Ic), formula (Id), formula (II), formula (II-1.1001) to formula (II-1.025), formula (II-2.001) to formula (II-2.018), formula (III), formula (IV), formula (V), formula (Va), formula (VI) or formula (VIa), that is essentially the pure (S)-enantiomer.

In one embodiment, the compositions of the present disclosure comprise a compound of formula (I), (Ia), (Ib), (Ic) or (Id) that is substantially enriched in an enantiomer. In another embodiment, the long-acting antiparasitic external devices of the present disclosure comprise a compound of formula (I), (Ia), (Ib), (Ic) or (Id) that is substantially enriched in the (S)-enantiomer. In another embodiment, the long-acting solid antiparasitic external devices of the present disclosure comprise a compound of formula (I), (Ia), (Ib), (Ic) or (Id) that is substantially enriched in the (R)-enantiomer.

In another embodiment of the present disclosure, the compositions comprise a compound of formula (I), (Ia), (Ib), (Ic) or (Id) that is enriched in the (S)-enantiomer in a weight:weight ratio is at least approximately 1.5:1 or 2:1 or greater. In yet another embodiment, the compositions of the present disclosure comprise a compound of formula (I), (Ia), (Ib), (Ic) or (Id) that is enriched in the (S)-enantiomer in a weight:weight ratio of at least about 5:1 or greater. In still another embodiment, the compositions of the present disclosure comprise a compound of formula (I), (Ia), (Ib), (Ic) or (Id) that is enriched in the (S)-enantiomer in a weight:weight ratio of at least approximately 10:1, 20:1, or greater. In still another embodiment, the compositions of the present disclosure comprise a compound of formula (I), (Ia), (Ib), (Ic) or (Id) that is essentially the pure (S)-enantiomer.

In another embodiment of the present disclosure, the compositions comprise a compound of formula (I), (Ia), (Ib), (Ic) or (Id) that is enriched in the (R)-enantiomer in a weight:weight ratio is at least approximately 2:1 or greater. In yet another embodiment, the compositions of the present disclosure comprise a compound of formula (I), (Ia), (Ib), (Ic) or (Id) that is enriched in the (R)-enantiomer in a weight:weight ratio of at least about 5:1 or greater. In still another embodiment, the compositions of the present disclosure comprise a compound of formula (I), (Ia), (Ib), (Ic) or (Id) that is enriched in the (R)-enantiomer in a weight:weight ratio of at least about 10:1, 20:1, or greater. In still another embodiment, the compositions of the present disclosure comprise a compound of formula (I), (Ia), (Ib), (Ic) or (Id) that is essentially the pure (R)-enantiomer.

In another embodiment of the present disclosure, the compositions comprise a compound of formula (II), formula (II-1.1001) to formula (II-1.025), formula (II-2.001) to formula (II-2.018), formula (III), formula (IV), formula (V), formula (Va), formula (VI) or formula (VIa), that is enriched in the (R)-enantiomer in a weight:weight ratio is at least approximately 2:1 or greater. In yet another embodiment, the compositions of the present disclosure comprise a compound of formula (II), formula (II-1.1001) to formula (II-1.025), formula (II-2.001) to formula (II-2.018), formula (III), formula (IV), formula (V), formula (Va), formula (VI) or formula (VIa), that is enriched in the (R)-enantiomer in a weight:weight ratio of at least about 5:1 or greater. In still another embodiment, the compositions of the present disclosure comprise a compound of formula (II), formula (II-1.1001) to formula (II-1.025), formula (II-2.001) to formula (II-2.018), formula (III), formula (IV), formula (V), formula (Va), formula (VI) or formula (VIa), that is enriched in the (R)-enantiomer in a weight:weight ratio of at least approximately 10:1, 20:1, or greater. In still another embodiment, the compositions of the present disclosure comprise a compound of formula (II), formula (II-1.1001) to formula (II-1.025), formula (II-2.001) to formula (II-2.018), formula (III), formula (IV), formula (V), formula (Va), formula (VI) or formula (VIa), that is essentially the pure (R)-enantiomer.

In another embodiment, the long-acting antiparasitic external devices of the present disclosure comprise an antiparasitic effective amount of at least one isoxazoline disclosed in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 WO 2008/122375, WO 2014/439475 A1 and WO2012 120135A1, all of which are incorporated herein by reference in their entirety.

In yet another embodiment, the long-acting antiparasitic external devices of present disclosure comprise an antiparasitic effective amount of at least one isoxazoline compound described in WO 2009/02451A2 and WO 2011/075591A1, both incorporated herein by reference in their entirety.

In one embodiment, the compositions of the present disclosure may comprise about 0.5 to about 50% (w/w) of an isoxazoline active agent of any of formulae (I), (Ia), (Ic), (Id), (II), (III), (IV), (V), (Va), (VI) or (VIa), or a pharmaceutically acceptable salt thereof, either as a racemic mixture or enriched in an enantiomer as described above. In another embodiment, the compositions of the present disclosure may comprise about 1 to about 40% (w/w) of an isoxazoline active agent of any of formulae (I), (Ia), (Ib), (Ic), (Id), (II), (III), (IV), (V), (Va), (VI) or (VIa), or a pharmaceutically acceptable salt thereof. In yet another embodiment, the compositions of the present disclosure may comprise about 1 to about 30% (w/w), about 1 to about 20% (w/w) or about 1 to about 15% (w/w) of an isoxazoline active agent of any of formulae (I), (Ia), (Ib), (Ic), (Id), (II), (III), (IV), (V), (Va), (VI) or (VIa), or a pharmaceutically acceptable salt thereof. In another embodiment, the compositions of the present disclosure may comprise about 0.5 to about 10% (w/w) or about 0.5% to about 5% (w/w) of an isoxazoline active agent of any of formulae (I), (Ia), (Ib), (Ic), (Id), (II), (III), (IV), (V), (Va), (VI) or (VIa), or a pharmaceutically acceptable salt thereof.

In another embodiment, the compositions of the present disclosure may comprise about 5 to about 40% (w/w) or about 5 to about 30% (w/w) of an isoxazoline active agent described herein, or a pharmaceutically acceptable salt thereof. In another embodiment, the compositions may comprise about 10% to about 40% (w/w) of an isoxazoline active agent described herein, or a pharmaceutically acceptable salt thereof. In yet another embodiment, the compositions of the present disclosure may comprise about 15% to about 40% (w/w), about 15% to about 35% (w/w) or about 15% to about 30% (w/w) of an isoxazoline compound, or a pharmaceutically acceptable salt thereof.

In embodiments, the long-acting solid antiparasitic external devices of present disclosure comprise one or more of the above-described compounds and compositions.

In certain embodiments the present disclosure provides for long-acting solid antiparasitic external devices for the treatment and/or prevention of parasitic infections and infestations in or on animals comprising:
  a) about 0.5 to 50% (w/w) of an isoxazoline active agent, such as, for example, any of the isoxazoline compounds provided for in the embodiments above (e.g., a compound of any of formula I to VIa described above), or a pharmaceutically acceptable salt thereof;
  b) an acceptable polymer matrix;
  c) optionally about 5% to about 50% (w/w) of one or more plasticizers; and
  d) optionally, about 0.01% to about 5.0% (w/w) of a pharmaceutically acceptable additive, excipient or mixtures thereof.

In another embodiment, the present disclosure provides for long-acting antiparasitic external devices comprising:
  a) about 0.5 to 40% (w/w) of an isoxazoline active agent, such as, for example, any of the isoxazoline compounds provided for in the embodiments above (e.g., a compound of any of formula I to VIa described above), or a pharmaceutically acceptable salt thereof;
  b) an acceptable polymer matrix;
  c) optionally about 5% to about 50% (w/w) of one or more plasticizers; and
  d) optionally, about 0.01% to about 5.0% (w/w) of a pharmaceutically acceptable additive, excipient or mixtures thereof.

In another embodiment, the present disclosure provides for long-acting antiparasitic external devices comprising:
  a) about 0.5 to 30% (w/w) of an isoxazoline active agent, such as, for example, any of the isoxazoline compounds provided for in the embodiments above (e.g., a compound of any of formula I to VIa described above), or a pharmaceutically acceptable salt thereof;
  b) an acceptable polymer matrix;
  c) optionally about 5% to about 50% (w/w) of one or more plasticizers; and
  d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prevention of parasitic infections and infestations in or on animals comprising:
  a) about 0.5 to 20% (w/w) of an isoxazoline active agent, such as, for example, any of the isoxazoline compounds provided for in the embodiments above (e.g., a compound of any of formula I to VIa described above), or a pharmaceutically acceptable salt thereof;
  b) an acceptable polymer matrix;
  c) optionally about 5% to about 50% (w/w) of one or more plasticizers; and
  d) optionally, about 0.01% to about 5.0% (w/w) of a pharmaceutically acceptable additive, excipient or mixtures thereof.

In certain embodiments the present disclosure provides for long-acting antiparasitic external devices for the treatment and/or prevention of parasitic infections and infestations in or on animals comprising:
  a) about 5 to 40% (w/w) of an isoxazoline active agent, such as, for example, any of the isoxazoline compounds provided for in the embodiments above (e.g., a compound of any of formula I to VIa described above), or a pharmaceutically acceptable salt thereof;
  b) an acceptable polymer matrix;
  c) optionally about 5% to about 50% (w/w) of one or more plasticizers; and
  d) optionally, about 0.01% to about 5.0% (w/w) of a pharmaceutically acceptable additive, excipient or mixtures thereof.

In another embodiment, the present disclosure provides for long-acting antiparasitic external devices comprising:

a) about 5 to 30% (w/w) of an isoxazoline active agent, such as, for example, any of the isoxazoline compounds provided for in the embodiments above (e.g., a compound of any of formula I to VIa described above), or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices comprising:
a) about 10 to 40% (w/w) of an isoxazoline active agent, such as, for example, any of the isoxazoline compounds provided for in the embodiments above (e.g., a compound of any of formula I to VIa described above), or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices comprising:
a) about 15 to 40% (w/w) of an isoxazoline active agent, such as, for example, any of the isoxazoline compounds provided for in the embodiments above (e.g., a compound of any of formula I to VIa described above), or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices comprising:
a) about 15 to 30% (w/w) of an isoxazoline active agent, such as, for example, any of the isoxazoline compounds provided for in the embodiments above (e.g., a compound of any of formula I to VIa described above), or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices comprising:
a) about 20 to 50% (w/w) of an isoxazoline active agent, such as, for example, any of the isoxazoline compounds provided for in the embodiments above (e.g., a compound of any of formula I to VIa described above), or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In certain embodiments the present disclosure provides for long-acting antiparasitic external devices for the treatment and/or prophylaxis of parasitic infections and infestations in or on animals comprising:

a) about 5 to about 50% (w/w) of an isoxazoline active agent of the formula (Ia), (e.g., a compound of formulae I-VIa), such as, a compound of the formula:

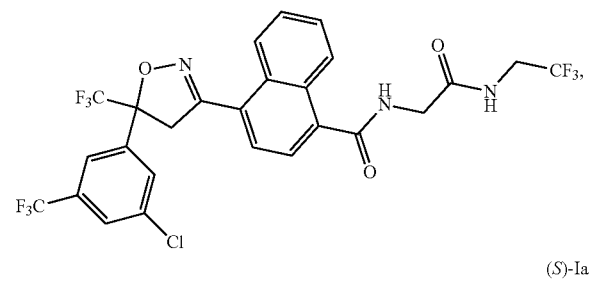

(Ia)

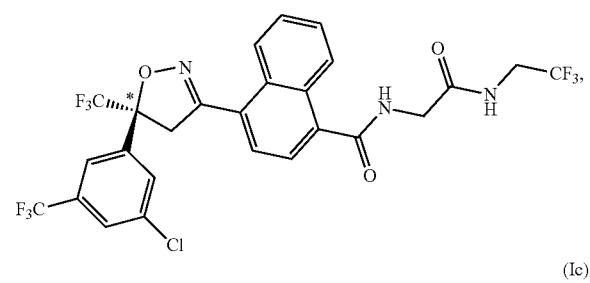

(S)-Ia

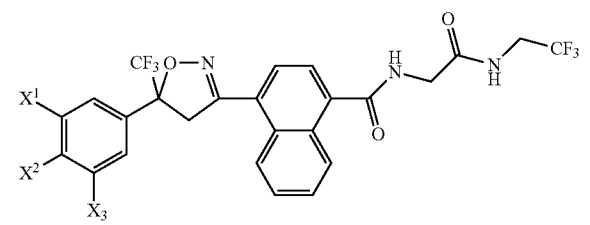

(Ic)

wherein $X^1$, $X^2$ and $X^3$ are independently chloro, fluoro or $CF_3$;

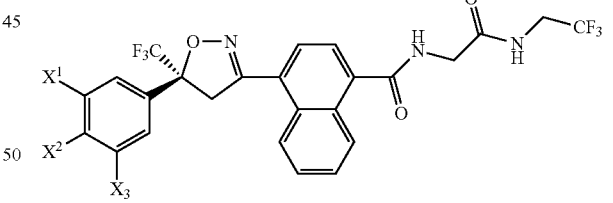

(S)-Ic wherein $X^1$, $X^2$ and $X^3$ are independently chloro, fluoro or $CF_3$;

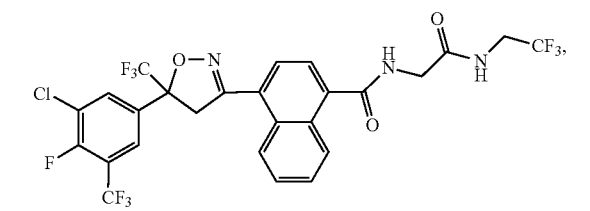

(Id)

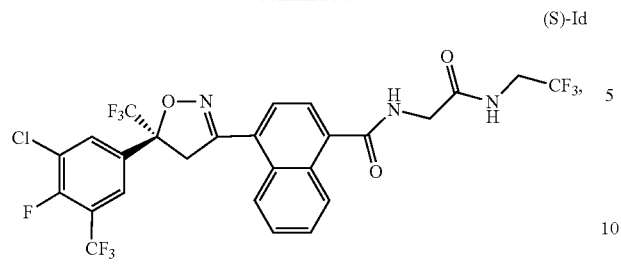
(S)-Id

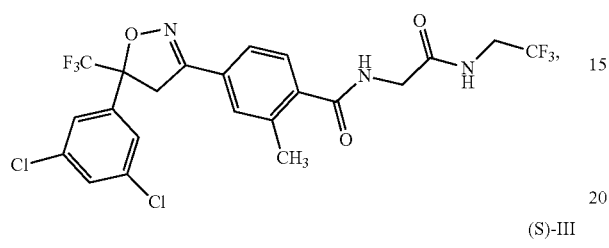
(III)

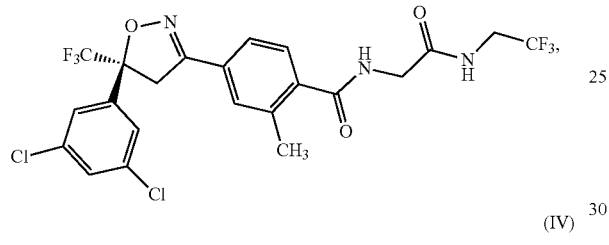
(S)-III

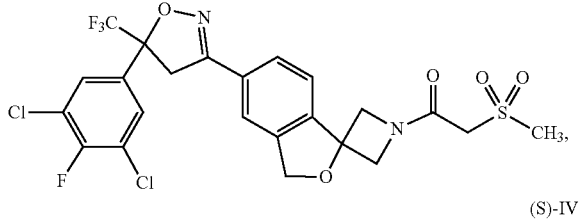
(IV)

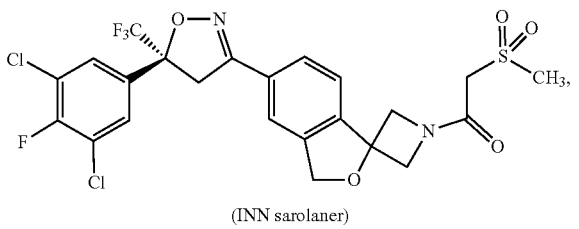
(S)-IV
(INN sarolaner)

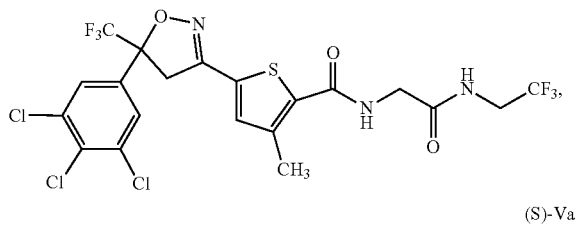
(Va)

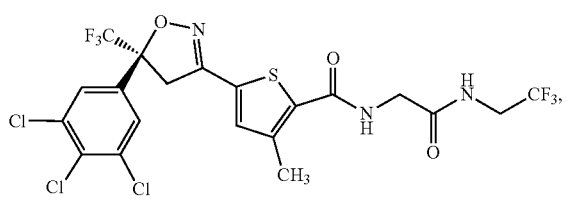
(S)-Va

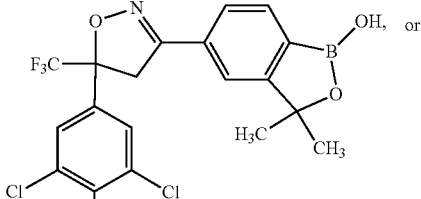
(VIa)

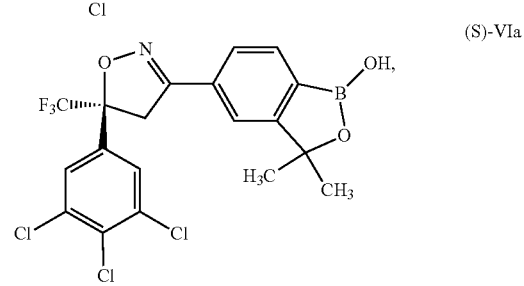
(S)-VIa or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In certain embodiments the present disclosure provides for long-acting antiparasitic external devices for the treatment and/or prophylaxis of parasitic infections and infestations in or on animals comprising:
a) about 1 to 40% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prophylaxis of parasitic infections and infestations in or on animals comprising:
a) about 1 to 30% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prophylaxis of parasitic infections and infestations in or on animals comprising:
a) about 1 to 20% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$; (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals comprising:
a) about 1 to 15% (w/w) of an isoxazoline active agent of the formula (Ia), (S)-Ia, (Ic), wherein $X^1$ is chloro, $X^2$ is fluoro and $X^3$ is $CF_3$; (S)-Ic, wherein $X^1$ is chloro, $X^2$ is fluoro and $X^3$ is $CF_3$; (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals comprising:
a) about 5 to 15% (w/w) of an isoxazoline active agent of the formula (Ia), (S)-Ia, (Ic), wherein $X^1$ is chloro, $X^2$ is fluoro and $X^3$ is $CF_3$; (S)-Ic, wherein $X^1$ is chloro, $X^2$ is fluoro and $X^3$ is $CF_3$; (Id) or (S)-Id, as shown above, or a pharmaceutically acceptable salt thereof,
b) an acceptable polymer matrix;
c) c) optionally about 5% to about 50% (w/w) of one or more plasticizers; and
d) optionally, about 0.01% to about 5.0% (w/w) of a pharmaceutically acceptable additive, excipient or mixtures thereof.

In certain embodiments the present disclosure provides for long-acting antiparasitic external devices for the treatment and/or prophylaxis of parasitic infections and infestations in or on animals comprising:
a) about 5 to 20% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals comprising:
a) about 10 to 30% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals comprising:
a) about 10 to 40% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments, the present disclosure provides for long-acting antiparasitic external devices for the treatment and/or prophylaxis of parasitic infections and infestation in or on animals comprising:
a) about 0.5 to about 50% (w/w) of an isoxazoline active agent of any of formulae (I), (Ia), (Ic), (Id), (II), (III), (IV), (V), (Va), (VI) or (VIa), or a pharmaceutically acceptable salt thereof, either as a racemic mixture or enriched in an enantiomer as described above. an isoxazoline agent or pharmaceutically acceptable salt thereof;
(b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices for the treatment and/or prophylaxis of parasitic infections and infestation in or on animals comprising:
a) about 1 to about 40% (w/w) of an isoxazoline active agent of any of formulae (I), (Ia), (Ib), (Ic), (Id), (II), (III), (IV), (V), (Va), (VI) or (VIa), or a pharmaceutically acceptable salt thereof;
(b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In yet another embodiment, the present disclosure provides for long-acting antiparasitic external devices for the treatment and/or prophylaxis of parasitic infections and infestation in or on animals comprising:
a) about 1 to about 30% (w/w), about 1 to about 20% (w/w) or about 1 to about 15% (w/w) of an isoxazoline active agent of any of formulae (I), (Ia), (Ib), (Ic), (Id), (II), (III), (IV), (V), (Va), (VI) or (VIa), or a pharmaceutically acceptable salt thereof.
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices for the treatment and/or prophylaxis of parasitic infections and infestation in or on animals comprising:
a) about 0.5 to about 10% (w/w) or about 0.5% to about 5% (w/w) of an isoxazoline active agent of any of formulae (I), (Ia), (Ib), (Ic), (Id), (II), (III), (IV), (V), (Va), (VI) or (VIa), or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices for the treatment and/or prophylaxis of parasitic infections and infestation in or on animals comprising:
a) about 5 to about 40% (w/w) or about 5 to about 30% (w/w) of an isoxazoline active agent described herein, or a pharmaceutically acceptable salt thereof.
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In another embodiment, the present disclosure provides for long-acting antiparasitic external devices for the treatment and/or prophylaxis of parasitic infections and infestation in or on animals comprising:
a) about 10% to about 40% (w/w) of an isoxazoline active agent described herein, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In yet another embodiment, the present disclosure provides for long-acting antiparasitic external devices for the treatment and/or prophylaxis of parasitic infections and infestation in or on animals comprising:
a) about 15% to about 40% (w/w), about 15% to about 35% (w/w) or about 15% to about 30% (w/w) of an isoxazoline compound, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

Another embodiment of the present disclosure provides for a long-acting antiparasitic external device for the treatment and/or prevention of parasitic infections and infestations in or on animals consisting essentially of:
a) an antiparasitic effective amount of at least one isoxazoline active agent, such as, for example, any of the isoxazoline compounds provided for in the embodiments above (e.g., a compound of formulae I-VIa), and optionally at least one additionally active agent as identified in this application;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 1 to 40% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prophylaxis of parasitic infections and infestations in or on animals consisting essentially of:
a) about 1 to 30% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prophylaxis of parasitic infections and infestations in or on animals consisting essentially of:
a) about 1 to 20% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$; (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 1 to 15% (w/w) of an isoxazoline active agent of the formula (Ia), (S)-Ia, (Ic), wherein $X^1$ is chloro, $X^2$ is fluoro and $X^3$ is $CF_3$; (S)-Ic, wherein $X^1$ is chloro, $X^2$ is fluoro and $X^3$ is $CF_3$; (Id) or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 5 to 15% (w/w) of an isoxazoline active agent of the formula (Ia), (S)-Ia, (Ic), wherein $X^1$ is chloro, $X^2$ is fluoro and $X^3$ is $CF_3$; (S)-Ic, wherein $X^1$ is chloro, $X^2$ is fluoro and $X^3$ is $CF_3$; (Id) or (S)-Id, as shown above, or a pharmaceutically acceptable salt thereof;

or a pharmaceutically acceptable salt thereof,
a) an acceptable polymer matrix;
b) c) optionally about 5% to about 50% (w/w) of one or more plasticizers; and
d) optionally, about 0.01% to about 5.0% (w/w) of a pharmaceutically acceptable additive, excipient or mixtures thereof.

In certain embodiments the present disclosure provides for long-acting antiparasitic external devices for the treatment and/or prophylaxis of parasitic infections and infestations in or on animals consisting essentially of:
a) about 5 to 20% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 10 to 30% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 10 to 40% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 5% to about 50% (w/w) of one or more plasticizers; and
d) optionally, about 0.01% to about 5.0% (w/w) of a pharmaceutically acceptable additive, excipient or mixtures thereof.

Another embodiment of the present disclosure is a long-acting antiparasitic external device for the treatment and/or prevention of parasitic infections and infestations in or on animals consisting essentially of:
a) an antiparasitic effective amount of at least one isoxazoline active agent, such as, for example, any of the isoxazoline compounds provided for in the embodiments above (e.g., a compound of formulae I-VIa), and optionally at least one additionally active agent as identified in this application;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 1 to 40% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, (Id) or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prophylaxis of parasitic infections and infestations in or on animals consisting essentially of:
a) about 1 to 30% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, (Id) or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In another embodiment the present disclosure provides for long-acting antiparasitic external devices for the treatment and/or prophylaxis of parasitic infections and infestations in or on animals consisting essentially of:
a) about 1 to 20% (w/w) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$; (Id) or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 1 to 15% (w/w) of an isoxazoline active agent of the formula (Ia), (S)-Ia, (Ic), wherein $X^1$ is chloro, $X^2$ is fluoro and $X^3$ is $CF_3$; (S)-Ic, wherein $X^1$ is chloro, $X^2$ is fluoro and $X^3$ is $CF_3$; (Id) or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 5 to 15% (w/w) of an isoxazoline active agent of the formula (Ia), (S)-Ia, (Ic), wherein $X^1$ is chloro, $X^2$ is fluoro and $X^3$ is $CF_3$; (S)-Ic, wherein $X^1$ is chloro, $X^2$ is fluoro and $X^3$ is $CF_3$; (Id) or (S)-Id, as shown above, or a pharmaceutically acceptable salt thereof;

or a pharmaceutically acceptable salt thereof,
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In certain embodiments the present disclosure provides for long-acting antiparasitic external devices for the treatment and/or prophylaxis of parasitic infections and infestations in or on animals consisting essentially of:
a) about 5 to 20% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 10 to 30% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In other embodiments the present disclosure provides for long-acting antiparasitic external devices for the treatment and/or prophylaxis of parasitic infections and infestations in or on animals consisting essentially of:
a) about 10 to 40% (w/w) of an isoxazoline active agent of the formula (S)-Ia, (S)-Ic, wherein $X^1$ is chloro, $X^2$ is fluoro and $X^3$ is $CF_3$; or (S)-Id, as shown above, or a pharmaceutically acceptable salt thereof;
b) an acceptable polymer matrix;
c) optionally about 1% to about 50% (w/w) of one or more plasticizers; and
d) optionally, about 0.01% to about 5.0% (w/w) of a pharmaceutically acceptable additive, excipient or mixtures thereof.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. The term "consisting of" excludes any element, step or ingredient not specified in the claims.

Definitions

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The expression "effective amount" as used herein means a concentration of the active agent in the composition sufficient to elicit the desired biological response to the target parasite(s) after administration of the composition to the animal, as measured by methods known in the art and/or described in the examples herein. In some embodiments, an "effective amount" of the active agent in the composition will provide an efficacy of at least 70% against the target parasite compared to an untreated control. In other embodiments, "an effective amount" of the active agent will provide an efficacy of at least 80%, or at least 85% compared to untreated controls. More typically, "an effective amount" of the active agent will provide an efficacy of at least 90%, at least 93%, at least 95% or at least 97% against the target parasite. In certain embodiments, the term "effective amount" may provide efficacy as high as 100%.

In certain embodiments, the expression "an effective amount" includes provision of a peak mean plasma concentration (Cmax) of the active agent. In certain embodiments the invention according to the present disclosure provides a Cmax of at least 50 ng/mL of the active agent. In other embodiments, the invention according to the present disclosure provides a Cmax of at least 10 or at least 20 ng/mL of the active agent. In other embodiments, the invention according to the present disclosure provides a Cmax of at least 15, at least 25, at least 30, at least 35, at least 40, or at least 45 ng/mL of the active agent.

The terms "treating" or "treat" or "treatment" are intended to mean the administration of a long-acting antiparasitic external device of the present disclosure to an animal that has a parasitic infestation for the eradication of the parasite or the reduction of the number of the parasites infesting the animal undergoing treatment. It is noted that the antiparasitic external device of the present disclosure may be used to prevent such a parasitic infestation.

The terms "prevent", "prevention" or "prophylaxis" are intended to mean the administration of the long-acting antiparasitic external device of the present disclosure to the animal before the parasitic infection or infestation has occurred in order to keep said infection or infestation from occurring. Prevention can also mean effectively killing parasites before they can reproduce, thereby effecting long-term control of said parasites. Administration of the long-acting antiparasitic external device at recommended regular intervals effectively prevents new parasitic infestations or infections in animals by killing new parasites that attack an animal before they can multiply to establish an infestation or infection.

The term "external device" refers to a solid composition comprising at least one polymeric matrix which is suitable for externally attaching to an animal including, for example, around the neck of the animal as a collar or as an ear tag, etc. An "antiparasitic external device" will contain one or more antiparasitic active agents in the device. In some embodiments the polymeric matrix may optionally contain other excipients including, but not limited to, one or more plasticizers, one or more stabilizers, one or more antioxidants, one or more lubricants, one or more fillers, one or more coloring agents, and the like. The external device may also contain a mixture of different polymeric matrices.

The term "acceptable polymer matrix" refers to a matrix of a polymer or mix of polymers that are safe for use on companion animals as an external wearable device. The acceptable polymer matrix will be suitably flexible to allow it to be affixed to the companion animal. Antiparasitic collars are well known in the art and an acceptable polymer matrix may utilize known polymers used in commercial antiparasitic collars. In other embodiments, an acceptable polymer matrix may contain polymers or polymer mixtures that are not typically used in commercial antiparasitic collars but are safe to administer to companion animals.

The term "essentially pure" is used herein to indicate that a compound or an enantiomer is at least about 90% pure, at least about 95%, at least about 98% pure, or higher.

The term "alkyl" refers to saturated straight, branched, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl" include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the present disclosure, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chloro-fluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkyl carbonyl," "alkoxycarbonyl," "alkyl aminocarbonyl," and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxy carb onyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkyl sulfonyl, alkenyl sulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl) amino, or trialkylsilyl.

The terms "aralkyl" or "arylalkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$)).

By the term "enriched" is meant when the weight:weight ratio is at least approximately 1.05 or higher in favor of the enantiomer that displays significant in vitro and in vivo activity (the eutomer).

Salts

Also contemplated within the scope of the present disclosure are acid or base salts, where applicable, of the compounds of the present disclosure provided for herein.

The term "acid salt" contemplates salts of the compounds with all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base salt" contemplates salts of the compounds with all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

In another embodiment, the long-acting antiparasitic external devices of present disclosure comprise an effective amount of at least one isoxazoline or a pharmaceutically acceptable salt thereof in combination at least one other active agent. In one embodiment, the long-acting antiparasitic external devices comprise an effective amount of at least one isoxazoline compound of formula (I) to (VI), or a pharmaceutically acceptable salt thereof, in combination with at least one other active agent.

Additional Veterinary/Pharmaceutical Active Ingredients

Additional veterinary/pharmaceutical active ingredients may be used with the compositions of the present disclosure. In some embodiments, the additional active agents may include, but are not limited to, acaricides, anthelmintics, antiparasitics and insecticides. Anti-parasitic agents can include both ectoparasiticidal and/or endoparasiticidal agents.

Veterinary pharmaceutical agents that may be included in the compositions of the present disclosure are well-known in the art (see e.g. *Plumb' Veterinary Drug Handbook*, 5th Edition, ed. Donald C. Plumb, Blackwell Publishing, (2005) or *The Merck Veterinary Manual*, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth sub salicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/− clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium·calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerin (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stiboglucon-ate, sodium sulfate, sodum thiosulfate, somatotropin, sotalol, spectinomycin, spironolactone, stanozolol, strepto-kinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the present disclosure, arylpyrazole compounds such as phenylpyrazoles, known in the art may be combined with the isoxazoline compounds in the long-acting antiparasitic external devices of the present disclosure. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, GA). In a particular embodiment, the antiparasitic external devices may include fipronil.

In another embodiment of the present disclosure, one or more macrocyclic lactones or lactams, which act as an acaricide, anthelmintic agent and/or insecticide, can be added to the antiparasitic external device compositions of the present disclosure.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, milbemycin oxime, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, GA).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alfa, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No.

4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alfa. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, New Jersey (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859, 657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment, the present disclosure comprises a long-acting antiparasitic external device composition comprising an isoxazoline compound in combination with compounds from a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225, 598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3 (2H)-one.

In an embodiment, the long-acting antiparasitic external devices of present disclosure comprise an effective amount of at least one isoxazoline of formula (I) to (VIa), or a pharmaceutically acceptable salt thereof, in combination with methoprene or pyriproxyfen.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumuron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoro-ethoxy)-phenylurea and 1-(2,6-difluorobenzoyl)-3-(2-fluoro-4-trifluoromethyl)phenylurea.

In yet another embodiment of the present disclosure, adulticide insecticides and acaricides can also be added to the long-acting antiparasitic external devices of the present disclosure. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, methiocarb, metolcarb, promacyl, propoxur, aldicarb, butocarboxim, oxamyl, thiocarboxime and thiofanox. In one embodiment, the compositions can include permethrin in combination with an isoxazoline active agent. In one embodiment, the compositions can include flumethrin in combination with an isoxazoline active agent. In one embodiment, the compositions can include deltamethrin in combination with an isoxazoline active agent.

In some embodiments, the long-acting antiparasitic external devices of the present disclosure may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, pyrantel, thiophanate and its o,o-dimethyl analogue may be included in the compositions.

In other embodiments, the long-acting antiparasitic external devices of the present disclosure may include an imidazothiazole compounds including, but not limited to, tetramisole, levamisole and butamisole. In still other embodiments, the long-acting compositions of the present disclosure may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the long-acting antiparasitic external devices of the present disclosure may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyluridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the long-acting antiparasitic external devices of the present disclosure of the present disclosure may include anti-trematodal agents. Suitable anti-trematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalane, oxyclozanide, diloxanide, rafoxanide, brotianide, bromoxanide and closantel; triclabendazole, diamfenetide, clorsulon, hetolin and emetine.

Anticestodal compounds may also be advantageously used in the long-acting compositions of the present disclosure of the present disclosure including, but not limited to, praziquantel, arecoline in various salt forms, bunamidine, niclosamide, nitroscanate, paromomycin and paromomycin II.

In yet other embodiments, the long-acting antiparasitic external devices of the present disclosure may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, di chl orenthi on, di emthoate, di oxathi on, ethi on, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethyl hexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with an isoxazoline compounds in the long-acting antiparasitic external device of the present disclosure can be a depsipeptides, which act at the neuromuscular junction by stimulating presynaptic receptors belonging to the secretin receptor family resulting in the paralysis and death of parasites. In one embodiment, the depsipeptide is a 24-membered cyclic depsipeptide isolated from the fungus *Mycelia sterilia* by Sasaki et al. (see *J. Antibiotics* 45: 692-697 (1992)) which have been found to exhibit broad anthelmintic activity against a variety of endoparasites in vivo with low toxicity. These compounds are described, for example, in U.S. Pat. Nos. 5,514,773; 5,747,448; 5,646,244; 5,874,530; among others, which are incorporated herein by reference. In one embodiment of the depsipeptide, the depsipeptide is emodepside (see Willson et al., *Parasitology*, January 2003, 126(Pt 1):79-86). In another embodiment, the depsipeptide is PF1022A or a derivative thereof. In other embodiments, the cyclic depsipeptide active agent is a compound described in U.S. Pat. Nos. 10,081,656 and 10,344,056, both incorporated herein by reference in their entirety.

In another embodiment, the long-acting antiparasitic external devices of the present disclosure may comprise an active agent from the neonicotinoid class of pesticides. The neonicotinoids bind and inhibit insect specific nicotinic acetylcholine receptors. In one embodiment, the neonicotinoid insecticidal agent that can be combined with an isoxazoline compound to form a long-acting antiparasitic external device of the present disclosure is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health and the oral soft-chewable composition Advantus™ from Piedmont Animal Health. Agents of this class are described, for example, in U.S. Pat. No. 4,742,060 or in EP 0 892 060. In another embodiment, the neonicotinoid active agent may be acetamiprid. In another embodiment, the solid antiparasitic external device of the invention may include the active agent nitenpyram. Nitenpyram is the active ingredient in the oral product CAPSTAR™ Tablets sold by Novartis Animal Health.

In yet another embodiment, the present disclosure provides the long-acting compositions of the present disclosure comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia) in combination with nitenpyram.

In yet another embodiment, the present disclosure provides the long-acting compositions of the present disclosure comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia) in combination with imidacloprid.

In certain embodiments, an insecticidal agent that can be combined with the long-acting compositions of the present disclosure is a semicarbazone, such as metaflumizone.

In another embodiment, the long-acting antiparasitic external devices of the present disclosure may advantageously include a combination of isoxazoline compounds known in the art. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the present disclosure, nodulisporic acid and its derivatives (a class of known acaricidal, anthelmintic, anti-parasitic and insecticidal agents) may be added to the long-acting antiparasitic external devices of the present disclosure. These compounds are used to treat or prevent infections in humans and animals and are described, for example, in U.S. Pat. No. 5,399,582, 5,962,499, 6,221,894 and 6,399,786, all of which are hereby incorporated by reference in their entirety. The antiparasitic external devices may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the long-acting antiparasitic external devices of the present disclosure. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 March 2008, 176-181.

The antiparasitic external devices of the present disclosure may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The long-acting antiparasitic external devices of the present disclosure may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the compositions of the present disclosure (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In general, the additional active agent is included in the long-acting antiparasitic external devices of the present disclosure in an amount of between about 0.1 µg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the present disclosure, the additional active agent may be included in the antiparasitic external devices to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 μg/kg to about 200 μg/kg or about 0.1 mg/kg to about 1 mg/kg of weight of animal. In still another embodiment of the present disclosure, the additional active agent is included in a dose between about 0.5 mg/kg to about 50 mg/kg.

Compositions

The antiparasitic external device of the invention comprises at least one polymer which is suitable to be attached to an external part of an animal. The polymer matrices must possess sufficient strength and pliability to ensure that they do not rupture or become brittle during manufacture and use. They must be of adequate durability to be resistant to normal wear and tear. In addition, the polymer matrices must allow adequate migration of the active compound to the surface of the device for delivery to the animal.

Within the scope of the present disclosure, matrices usually used to make antiparasitic collars may be used. Elastomers (particularly thermoelastomers) and thermoplastics including, for example, flexible thermoplastic polyolefins, are suitable for use as a carrier substance or basis for the antiparasitic external device. Thermoelastomers and thermoplastics are most suitable for use as a polymer matrix for the antiparasitic external device of the invention as herein described.

As would be understood by one skilled in the art, thermoelastomers and thermoplastics are polymers that are thermally processable such as by extrusion or injection molding. Those which may be mentioned are polyesters, polyvinyl resins, and acrylic polymers, including polyvinyl resins such as polyvinyl chloride (PVC) and vinyl chloride copolymers, polyethylene (e.g. HDPE or LLDPE) and polypropylene, EPDM (ethylene-propylene-diene terpolymer), polyvinyl acetate (PVAc), ethylene-vinyl acetate copolymers (EVA), polystyrene (PS) and copolymers, which are sufficiently compatible with the abovementioned active compounds. In another embodiment, the external device compositions of the invention comprises polyesters such as polybutylene succinate (PBS), polybutylene succinate adipate (PB SA), polylactide (PLA), polylactide-glycolide (PLGA), polycaprolactone (PCL), polyhydroxyalkanoate (PHA) and polybutylene adipate terephthalate (PBAT).

In one embodiment PVC (polyvinyl chloride), as described in U.S. Pat. Nos. 3,318,769, 3,852,416 and 4,150,109 and 5,437,869 (all incorporated herein by reference), and other vinyl polymers may be used to prepare the antiparasitic external devices of the invention. The polyvinyl resins include polyvinyl halides, such as polyvinyl chloride, polyvinyl chloride-vinyl acetate and polyvinyl fluoride; polyvinylbenzenes, such as polystyrene and polyvinyltoluene. In some embodiments, polyvinyl chloride, polypropylene, polyethylene, and EPDM may be utilized. Other plastics (i.e. polymers) which are suitable for use as matrix for the antiparasitic external device according to the present disclosure are thermoplastic elastomers. These are materials which contain elastomeric phases which are either physically incorporated or chemically bonded in thermoplastically processable polymers. A distinction is made from polymer blends, in which the elastomeric phases are a component of the polymeric skeleton. As a result of the constitution of the thermoplastic elastomers, hard and soft regions are present alongside each other. In this connection, the hard regions form a crystalline reticular structure or a continuous phase whose interstices are filled with elastomeric segments. Because of this constitution, these materials have rubber-like properties. In this connection, reference may be made to thermoplastic polyolefins (TPO) and to styrene block copolymers (see, for example, EP 542078).

Polymers matrices that may be used in the present invention include, but are not limited to the following:
1. Vinyl polymers: include but not limited to polyvinyl chloride (PVC); polyvinylidene chloride (PVDC); polyvinylidene fluoride (PVDF); polyethylene (PE); polypropylene (PP); chlorinated polyethylene (CPE); chlorinated polypropylene (CPP); ethylene-propylene copolymers; polyvinyl acetate (PVAc); ethylene-vinyl acetate copolymer (EVA); polyvinyl chloride-vinyl acetate; polyvinyl fluoride; polystyrene and polystyrene copolymers; polyisobutylene (PIB); styrene-butadiene rubber (SBR); styrene-isoprene rubber (SIS);
2. Polyesters: polyethylene terephthalate (PET) and copolymers; polylactide (PLA) and copolymers, polylactide-co-glycolide) (PLGA); polycaprolactone (PCL) and copolymers; polyhydroxyalkanoates (PHAs); polybutylene succinate (PBS); polybutylene succinate-co-adipate (PBSA); and polybutylene adipate terephthalate (PBAT);
3. Nylons: including but not limited to Nylon 6; Nylon 66; Nylon 12;
4. Polyacrylates, Polymethacrylates, and methacrylate and acrylate copolymers: including but not limited to polymethyl methacrylate (PMMA); polymethyl acrylate (PMA); polyethyl methacrylate (PEMA); polybutyl methacrylate (PBMA); and their copolymers;
5. Biopolymers: Cellulosic polymers such as cellulose acetate (CA); ethylcellulose (EC), etc.
6. Polymer blends: any combinations of polymer blends containing one or more of any of the above individual polymers.

In certain embodiments, an antiparasitic external device according to the present disclosure includes a polymer matrix containing at least one polymer that is a vinyl polymer, a polyester, a nylon, a polyacrylate (or polymethacrylcate), a cellulosis polymer, or a thermoplastic polyurethane.

In some embodiments of the antiparasitic device according to the present disclosure, the vinyl polymer comprises polyvinyl chloride (PVC), polyvinylidene chloride (PVDC), polyvinylidene fluoride (PVDF), polyethylene (PE), polypropylene (PP), chlorinated polyethylene (CPE), chlorinated polypropylene (CPP), ethylene-propylene copolymers, polyvinyl acetate (PVAc), ethylene-vinyl acetate copolymer (EVA), polyvinyl chloride-vinyl acetate, polyvinyl fluoride, polystyrene, polyisobutylene (PM), styrene-butadiene rubber (SBR), styrene-isoprene rubber (SIS), or a combination thereof.

In some embodiments of the antiparasitic device according to the present disclosure, the polyester comprises polyethylene terephthalate (PET), a PET copolymer, a polylactide (PLA), a PLA copolymer, polylactide-co-glycolide (PLGA), polycaprolactone (PCL), a PCL copolymer, a polyhydroxyalkanoate (PHA), polybutylene succinate (PBS), a polybutylene succinate-co-adipate (PBSA), a polybutylene adipate terephthalate (PBAT), or a combination thereof.

In some embodiments of the antiparasitic device according to the present disclosure, the polymer matrix comprises a biodegradable polyester selected from polybutylene succinate (PBS); polybutylene succinate-co-adipate (PBSA); polylactide (PLA) and/or copolymers; polylactide-co-glycolide) (PLGA); polycaprolactone (PCL), PCL copolymer, a polyhydroxyalkanoate (PHA), a polybutylene adipate terephthalate (PBAT), or combinations thereof. In some embodiments, the polymer matrix preferably comprises a biodegradable polyester. In certain embodiments the biodegradable polyester is polybutylene succinate-co-adipate (PBSA), and/or polybutylene succinate (PBS), and/or polybutylene adipate terephthalate (PBAT).

In some embodiments of the antiparasitic device according to the present disclosure, the polymer matrix comprises a nylon selected from the group consisting of Nylon 6, Nylon 66, and Nylon 12.

In some embodiments of the antiparasitic device according to the present disclosure, the polymer matrix comprises at least one polyacrylate or a polymethacrylate selected from the group consisting of polymethyl methacrylate (PMMA), polymethyl acrylate (PMA), polyethyl methacrylate (PEMA), polybutyl methacrylate (PBMA), and their copolymers.

In some embodiments of the antiparasitic device according to the present disclosure, the polymer matrix comprises a cellulosic polymer that is cellulose acetate (CA) and/or ethylcellulose (EC).

In certain embodiments of the antiparasitic device according to the present disclosure, the polymer matrix comprises any one of polyvinyl acetate (PVAc), ethylene-vinyl acetate copolymer (EVA), polyvinyl chloride-vinyl acetate, or a mixture thereof. In one embodiment, the polymer matrix preferably comprises any one of polyvinyl acetate (PVAc), ethylene-vinyl acetate copolymer (EVA), polyvinyl chloride-vinyl acetate, or a mixture thereof. In yet another embodiment, the polymer matrix preferably comprises or consists of ethylene-vinyl acetate copolymer (EVA).

In embodiments, plasticizers may be used for softening the pharmaceutically acceptable polymer. For example, plasticizers may be used for softening solid vinyl resins for producing the antiparasitic external devices based on polyolefins, in particular polyvinyl resins. The plasticizer to be used depends on the resin and on its compatibility with the plasticizer. Examples of suitable plasticizers are adipates, phthalates, phosphates and citrates, such as phosphoric acid esters and adipic acid esters, such as diiso- and n-butyl adipate, for example. It is also possible to use other esters, such as the esters of azelaic acid, maleic acid, ricinoleic acid, myristic acid, palmitic acid, oleic acid, sebacic acid, stearic acid and trimellitic acid, as well as complex linear polyesters, polymeric plasticizers and epoxidized soybean oils.

In embodiments, one or more plasticizers will preferably be added to a PVC based matrix, these plasticizers being chosen in particular from the following compounds; diethyl phthalate, bis-(2-ethylhexyl)phthalate (DEHP), dioctyl sebacate, dioctyl adipate, diisodecyl phthalate, acetyl tributyl citrate, diethylhexyl phthalate, di-n-butyl phthalate, benzyl butyl phthalate, acetyl tributyl citrate, tricresyl phosphate, and 2-ethylhexyl diphenyl phosphate.

In other embodiments, a PVC based matrix will be used in the presence of a primary remanent plasticizer and a secondary plasticizer, such as acetyl triethyl citrate, triethyl citrate, triacetin, diethylene glycol monoethyl ether, and triphenyl phosphate.

In embodiments plasticizers are employed in quantities of from about 5 to 50% by weight. In some embodiments, plasticizers are employed in quantities of from about 1 to 50% by weight. In other embodiments plasticizers are employed in quantities of from about 15 to 45% by weight, of the total composition. In yet other embodiments, plasticizers are employed in quantities of from about 5 to 45% by weight of the total composition. In yet other embodiments, the plasticizer may be included in concentrations of about 5 to about 30%, about 5 to about 25% or about 5 to about 20% by weight. In still other embodiments, the plasticizer may be employed in a concentration of about 5 to about 15 or about 5 to about 10% by weight. In another embodiment, the plasticizer may be included in a concentration of about 20 to about 40% by weight or about 25 to about 35% by weight of the composition.

In other embodiments, the antiparasitic external devices also comprise at least one additional constituent selected from stabilizers, lubricants, mold-release agents, fillers, and coloring materials. Suitable stabilizers are antioxidants and agents which protect the external devices from ultraviolet radiation and undesirable breakdown during the processing, such as extruding. Some stabilizers, such as epoxidized soybean oils, also serve as secondary plasticizers. Examples of lubricants which can be used are stearates (e.g. zinc stearate), stearic acid and low molecular weight polyethylenes.

In embodiments the additional constituents comprise up to about 10% by weight of the total composition. In one embodiment, the amount of additional constituents may comprise about 1 to about 10% or about 2 to about 8% by weight of the composition. In yet another embodiment, the concentration of additional constituents may comprise about 1 to about 5% by weight or about 2 to about 6% by weight.

In embodiments, the antiparasitic collar or other antiparasitic external device may comprise two or more polymeric matrices, wherein each matrix may vary by concentration and/or composition. By using a collar or other external device according to the present disclosure comprising two or more polymeric matrices, delivery of two or more active agents may be accomplished, which allows for effective and long-lasting protection against ectoparasites (e.g. fleas and ticks) and in certain embodiments protection against endoparasites that harm animals. Using two or more polymeric matrices may also be desirable for purposes of drug compatibility, drug release profile, superior mechanical property, cost, and more.

Further, by utilizing two or more polymeric matrices with varying concentration and/or composition, it is possible to make collars or other external devices according to the present disclosure which ensure effective and long-lasting protection against ectoparasites (e.g. fleas and ticks) and in certain embodiments may also be active against endoparasites that harm animals. In one embodiment of the invention, blends of two or more polymers may be used in the antiparasitic external device compositions. The blending of polymers having different affinity for the active agent(s) included in the compositions may be used to modify the rate of release of the active agent(s) from the polymer matrix. This may be used to shorten or extend the duration of efficacy of the antiparasitic compositions.

The antiparasitic collars or other antiparasitic external devices of the invention may be made to produce an efficacy of at least 70% against ectoparasites of greater than 3, 6, 8 or 9 months. In other embodiments, the antiparasitic collar or antiparasitic external devices of the invention provide an efficacy of at least 80% or at least 90% against ectoparasites for at least 3, 6, 8 or 9 months. In yet another embodiment, the antiparasitic collar or antiparasitic external devices of the invention provide an efficacy of at least 95% against ectoparasites for at least 3, 6, 8 or 9 months. In some embodiments, the collars of the invention may provide efficacy against parasites up to 12 or 15 months, even when the collar or external device is taken off for a relatively prolonged period. When the collar or external device is taken off, the duration of effective protection of the animal may still range from 1 to 2 additional months.

Generally, when the antiparasitic external devices of the invention are produced, the different constituents are mixed in accordance with known methods and molded in accordance with extrusion and injection molding methods known in the art. The choice of the processing method for producing the external devices depends technically in principle on the rheological properties of the polymeric matrix and on the shape of the desired antiparasitic external device. In embodiments, the process for producing the external devices of the invention may include one or more of the following methods; casting, injection-molding, extruding, calendering, rolling, kneading, stamping, bending, and thermoforming.

Applying a coating to the antiparasitic external devices of the invention is contemplated.

For the purposes of the present disclosure, the term external device should be understood to refer to any device which can be attached externally to the animal in order to provide the same function as a collar. By varying the concentration and/or composition of the matrix, antiparasitic collars or other antiparasitic external devices according to the present disclosure, which allow effective and long-lasting protection against fleas and ticks, may be made. Antiparasitic collars or other antiparasitic external devices may be made with an efficacy of at least 3, 6, 8 or 9 months, in particular of greater than or equal to 12 or 15 months, even when the antiparasitic collar or other antiparasitic external device is taken off for a relatively prolonged period. When the antiparasitic collar or other antiparasitic external device is taken off, the duration of effective protection may continue to last, in some embodiments in the range from 1 to 2 months.

The long-acting antiparasitic external devices of the present disclosure may include pharmaceutically acceptable additives or excipients. Pharmaceutically acceptable additives and excipients include, but are not limited to, colorant, filler, surfactants, antioxidants, UV stabilizer, preservatives, pH stabilizing agents (e.g. buffers), lubricant, flow agent, and other non-active excipients. In another embodiment, the antiparasitic external devices of the present disclosure may comprise about 0.01% to about 20% (w/w) of a pharmaceutically acceptable additive, excipient or mixtures thereof. In other embodiments, the antiparasitic external devices may comprise about 0.01% to about 5% (w/w), about 0.1% to about 10% (w/w) or about 0.1% to about 5% (w/w) of a pharmaceutically acceptable additive, excipient or mixtures thereof. In other embodiments the antiparasitic external devices may comprise about 5 to about 15% (w/w) or about 5 to about 10% (w/w) of a pharmaceutically acceptable additive, excipient or mixtures thereof. In yet another embodiment, the antiparasitic external devices may comprise about 7 to about 10% of a pharmaceutically acceptable additive, excipient or mixtures thereof.

The novel and inventive antiparasitic external devices may contain other inert ingredients such as antioxidants, preservatives, or pH stabilizers. These compounds are well known in the composition art. Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy-anisole), BHT (butylated hydroxy toluene), BHA and citric acid, monothioglycerol, tert-butyl hydroquinone (TBHQ), and the like, may be added to the present antiparasitic external devices. The antioxidants are generally included in the antiparasitic external devices of the present disclosure in amounts of about 0.01% to about 3%, or from about 0.01 to about 2% (w/w), based upon total weight of the antiparasitic external device (w/w). In another embodiment, the antiparasitic external devices contain about 0.05 to about 1.0% (w/w) of one or a mixture of antioxidants.

Preservatives, such as the parabens (methylparaben and/or propylparaben), are suitably used in the composition in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the composition are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate.

Compounds which affect the release of the active agent from the antiparasitic external device are also contemplated.

Dosage forms may contain from about 0.5 mg to about 5 g of an active agent or a combination of active agents. More typically, the amount of active agent(s) in the antiparasitic external devices of the present disclosure will be from about 1 mg to about 3 g. In another embodiment, the amount of active agent(s) in the antiparasitic external devices will be from about 20 mg to about 3 g. In another embodiment, the amount of active agent(s) present in the antiparasitic external devices will be from about 20 mg to about 2 g, about 20 mg to about 1.5 g or about 20 mg to about 1 g. In other embodiments, the amount of active agent(s) in the antiparasitic external devices will be from about 20 mg to about 500 mg, about 30 mg to about 200 mg or about 50 mg to about 200 mg. In still another embodiment, the amount of active agent(s) present in the antiparasitic external devices will be from about 50 mg to about 2 g, about 50 mg to about 1 g or about 50 mg to about 500 mg. In yet another embodiment of the present disclosure, the about of active agent(s) present will be from about 100 mg to about 2 g, about 100 mg to about 1 g or about 100 mg to about 500 mg.

In another embodiment, the amount of active agent(s) present in the antiparasitic external devices of the present disclosure is from about 1 mg to about 500 mg of an active agent, about 1 mg to about 100 mg or about 1 mg to about 25 mg. In still other embodiments, the amount of the active agent present in the antiparasitic external devices is about 10 mg about 50 mg or about 10 mg to about 100 mg. In other embodiments, the amount of active agent present in the antiparasitic external devices is about 50 mg to about 200 mg, about 100 mg to about 300 mg, about 100 mg to about 400 mg, about 200 mg to about 500 mg, about 300 mg to about 600 mg, about 400 mg to about 800 mg, or about 500 mg to about 1000 mg. In some embodiments, the amount of active agent(s) present in the antiparasitic external devices of the present disclosure is preferably more than 1000 mg, more than 2000 mg, more than 3000 mg, more than 4000 mg, and more than 5000 mg, such as about 5500 mg, or more than 5500 mg.

Many collars weight about 20-50 g, thus an active that comprises about 11% (w/w) of the collar as herein exemplified is the equivalent of about 5.5 g or 5500 mg of the active agent. Thus, in some embodiments, the amount of active agent(s) present in the antiparasitic external devices of the present disclosure is about 1 to 40% (w/w) of at least one isoxazoline active agent. In yet other embodiments, the amount of active agent(s) is about 1 to 30% (w/w), about 1 to 20% (w/w), and about 1 to 15% (w/w).

In one embodiment, the antiparasitic external device of the invention (e.g. parasitic collar) may comprise about 1 to about 40% (w/w) at least one isoxazoline active agent such as those described above, about 30 to about 80% (w/w) of a polyvinyl polymer, about 1 to about 40% (w/w) or about 10 to about 40% (w/w) of a plasticizer, and optionally about 0.5 to about 5% (w/w) of a stabilizer, lubricant, and one or more pharmaceutically acceptable additives or excipients.

In another embodiment, the antiparasitic external device of the invention (e.g. parasitic collar) may comprise about 5 to about 30% (w/w) at least one isoxazoline active agent such as those described above, about 40 to about 70% (w/w) of a polyvinyl polymer, about 5 to about 35% (w/w) or about 15 to about 35% (w/w) of a plasticizer, and optionally about 0.5 to about 5% (w/w) of a stabilizer, lubricant, and one or more pharmaceutically acceptable additives or excipients.

In another embodiment, the antiparasitic external device of the invention (e.g. parasitic collar) may comprise about 5 to about 20% (w/w) at least one isoxazoline active agent such as those described above, about 45 to about 65% (w/w) of a polyvinyl polymer, about 15 to about 35% (w/w) or about 25 to about 35% (w/w) of a plasticizer, and optionally about 0.5 to about 5% (w/w) of a stabilizer, lubricant, and one or more pharmaceutically acceptable additives or excipients.

In one embodiment, the antiparasitic external device of the invention (e.g. parasitic collar) may comprise about 1 to about 40% (w/w) at least one isoxazoline active agent such as those described above, about 30 to about 80% (w/w) of a polymer, about 1 to about 40% (w/w) of a plasticizer, and optionally about 0.5 to about 5% (w/w) of a stabilizer, lubricant, and one or more pharmaceutically acceptable additives or excipients.

In another embodiment, the antiparasitic external device of the invention (e.g. parasitic collar) may comprise about 5 to about 30% (w/w) at least one isoxazoline active agent such as those described above, about 40 to about 70% (w/w) of a polymer, about 5 to about 35% (w/w) of a plasticizer, and optionally about 0.5 to about 5% (w/w) of a stabilizer, lubricant, and one or more pharmaceutically acceptable additives or excipients.

In another embodiment, the antiparasitic external device of the invention (e.g. parasitic collar) may comprise about 5 to about 20% (w/w) at least one isoxazoline active agent such as those described above, about 45 to about 65% (w/w) of a polymer, about 15 to about 35% (w/w) of a plasticizer, and optionally about 0.5 to about 5% (w/w) of a stabilizer, lubricant, and one or more pharmaceutically acceptable additives or excipients.

In one embodiment, the antiparasitic external device of the invention (e.g. parasitic collar) may comprise about 5 to about 20% (w/w) at least one isoxazoline active agent of formula (I) described above, about 45 to about 65% (w/w) of a polyvinyl chloride (PVC) polymer, about 25 to about 35% (w/w) of a phthalate plasticizer, and about 1 to about 5% (w/w) of a stabilizer, lubricant (e.g. a stearate) and one or more pharmaceutically acceptable additives or excipients.

In one embodiment, the antiparasitic external device of the invention (e.g. parasitic collar) may comprise about 5 to about 20% (w/w) the isoxazoline active agent of formula (Ia) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula (Ib) described above, about 45 to about 65% (w/w) of a polyvinyl chloride (PVC) polymer, about 25 to about 35% (w/w) of a phthalate plasticizer, and about 1 to about 5% (w/w) of a stabilizer, lubricant such as a stearate and one or more pharmaceutically acceptable additives or excipients.

In one embodiment, the antiparasitic external device of the invention (e.g. parasitic collar) may comprise about 5 to about 20% (w/w) at least one isoxazoline active agent of formula (Ic) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) the isoxazoline active agent of formula (Id) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula (II) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula II-1.001 to II-1.025 described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula II-2.001 to II-2.018 described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) the isoxazoline active agent of formula (III) described above, about 45 to about 65% (w/w) of a polyvinyl chloride (PVC) polymer, about 25 to about 35%

(w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) the isoxazoline active agent of formula (IV) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula (V) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) the isoxazoline active agent of formula (Va) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula (VI) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) the isoxazoline active agent of formula (VIa) described above, about 45 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) the isoxazoline active agent of formula (S)-Ia described above, about 50 to about 65% (w/w) of a polyvinyl chloride (PVC) polymer, about 25 to about 35% (w/w) of a phthalate plasticizer, about 1 to about 5% (w/w) of a stabilizer or lubricant such as a stearate and optionally one or more pharmaceutically acceptable additives or excipients.

In one embodiment, the antiparasitic external device of the invention (e.g. parasitic collar) may comprise about 5 to about 20% (w/w) at least one isoxazoline active agent of formula (I) described above, about 65 to about 95% (w/w) of a polybutylene succinate-co-adipate (PBSA) polymer, about 0 to about 35% (w/w) of a plasticizer, and about 0 to about 5% (w/w) of one or more pharmaceutically acceptable additives or excipients.

In one embodiment, the antiparasitic external device of the invention (e.g. parasitic collar) may comprise about 5 to about 20% (w/w) at least one isoxazoline active agent of formula (I) described above, about 65 to about 95% (w/w) of a polybutylene succinate (PBS) polymer, about 0 to about 35% (w/w) of a plasticizer, and about 0 to about 5% (w/w) of one or more pharmaceutically acceptable additives or excipients.

In one embodiment, the antiparasitic external device of the invention (e.g. parasitic collar) may comprise about 5 to about 20% (w/w) at least one isoxazoline active agent of formula (I) described above, about 65 to about 95% (w/w) of a ethylene-vinyl acetate co-polymer (EVA), about 0 to about 15% (w/w) of a plasticizer, and about 0 to about 5% (w/w) of one or more pharmaceutically acceptable additives or excipients.

In one embodiment, the antiparasitic external device of the invention (e.g. parasitic collar) may comprise about 5 to about 20% (w/w) at least one isoxazoline active agent of formula (I) described above, about 65 to about 95% (w/w) of a ethylene-vinyl acetate co-polymer (EVA) with a vinyl acetate (VA) content from 5 to 40%, about 0 to about 15% (w/w) of a plasticizer, and about 0 to about 5% (w/w) of one or more pharmaceutically acceptable additives or excipients.

In one embodiment, the invention according to the present disclosure provides for an antiparasitic external device for the treatment and/or prevention of a parasitic infestation or infection in an animal comprising
i) an effective amount of a least one parasiticidal active agent which is a compound of formula (Ia) or (Id):

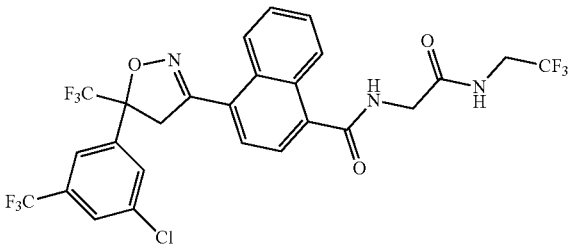

(Ia)

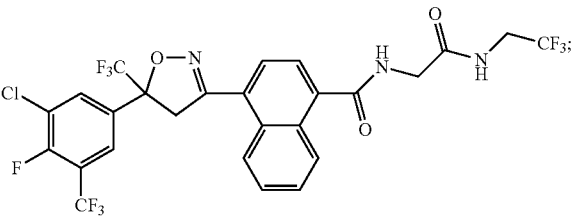

(Id)

ii) a polymer matrix which consists of at least one of polybutylene succinate (PBS), polybutylene succinate adipate (PBSA), ethylene-vinyl acetate copolymer (EVA), and polyvinyl chloride;
iii) optionally, a plasticizer; and
iv) optionally, a stabilizer and/or an antioxidant.

In another embodiments, the invention according to the present disclosure provides an antiparasitic external device for the treatment and/or prevention of a parasitic infestation or infection in an animal comprising
i) an effective amount of a least one parasiticidal active agent which is a compound of formula (Ia) or (Id):

(Ia)

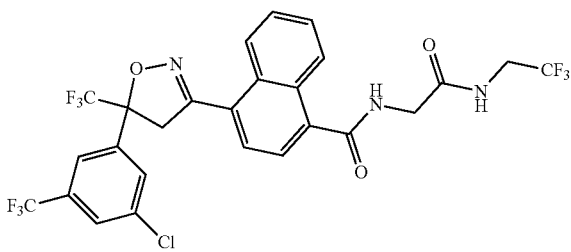

(Id)

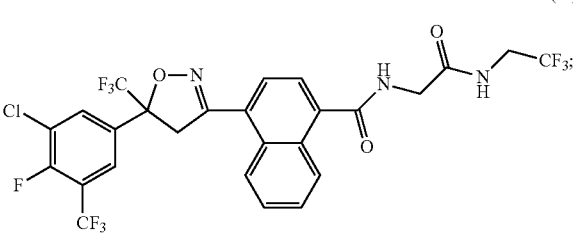

ii) a polymer matrix which consists of ethylene-vinyl acetate copolymers (EVA) with 5 to 95% vinyl acetate;
iii) optionally, a plasticizer; and
iv) optionally, a stabilizer and/or an antioxidant.

In certain embodiments according to the invention, the aforementioned EVA polymer matrix contains 10-50% vinyl acetate; in another embodiment the vinyl acetate content is preferably 10-30%; in yet another embodiment, the vinyl acetate content is about 12%.

In certain embodiments according to the invention, the aforementioned EVA polymer matrix contains 5-50% vinyl acetate; in another embodiment the vinyl acetate content is preferably 5-30%; in yet another embodiment, the vinyl acetate content is about 12%.

In certain embodiments of the antiparasitic external device of the invention, the polymer matrix consists of polybutylene succinate. In certain embodiments, the antiparasitic external device of the invention does not include a plasticizer.

In another embodiment of the antiparasitic external device of the invention, the polymer matrix consists of polybutylene succinate, and the antiparasitic external device includes a plasticizer; in one embodiment, the polymer matrix consists of polybutylene succinate with triethyl citrate, such as about 10% triethyl citrate, as a plasticizer.

In one embodiment, the invention according to the present disclosure provides an antiparasitic external device for the treatment and/or prevention of a parasitic infestation or infection in an animal comprising
  i) an effective amount of a least one parasiticidal active agent which is a compound of formula (Ia) or (Id):

(Ia)

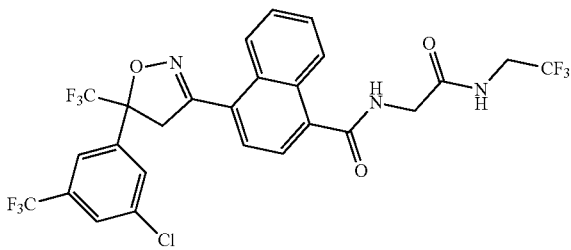

(Id)

ii) a polymer matrix which consists of at of polybutylene succinate adipate (PBSA);
iii) optionally, a plasticizer; and
iv) optionally, a stabilizer and/or an antioxidant.

Methods of Treatment

In another aspect of the present disclosure, a method for preventing and/or treating a parasite infestation and/or infection in an animal is provided, comprising administering to the animal a long-acting antiparasitic external device of the invention comprising an effective amount of at least one isoxazoline compound, a pharmaceutically acceptable polymer matrix, and optionally, a plasticizer, an antioxidant, pharmaceutically acceptable additive and/or excipient. The compositions of the present disclosure have long-lasting efficacy against ectoparasites (e.g. fleas and ticks) and in certain embodiments when combined with other active agents may also be active against endoparasites that harm animals.

The compositions of the present disclosure are administered/released from the antiparasitic external devices of the present disclosure in parasiticidally effective amounts which are suitable to control the parasite in question to the desired extent, as described below. In each aspect of the present disclosure, the compounds and compositions of the present disclosure released from the antiparasitic external devices can be applied against a single pest or combinations thereof.

In some embodiments for companion animals, the dose of the isoxazoline active agent administered from the antiparasitic external devices of the present disclosure is between about 0.1 to about 50 mg per kg of body weight. More typically the dose of the isoxazoline active agent administered is about 0.5 to about 30 mg/kg or about 0.5 to about 30 mg/kg body weight. In yet another embodiment, the dose of the isoxazoline active agent will be from about 0.5 to about 20 mg/kg, about 0.5 to about 10 mg/kg or about 0.5 to about 5 mg/kg body weight. In another embodiment, the dose will be from about 0.5 to about 2.5 mg/kg body weight. In another embodiment, the dose of the isoxazoline active agent administered is about 10 to about 30 mg/kg, about 15 to about 30 mg/kg or about 20 to about 30 mg/kg of body weight.

In other embodiments, the dose administered may be lower depending on the animal and the isoxazoline administered. For example, if the antiparasitic external device comprises the more active enantiomer of the isoxazoline compounds a lower dose may be administered. In some embodiments, the dose is from about 0.1 to about 30 mg/kg of body weight. In another embodiment, the dose may be from about 0.1 to about 20 mg/kg or about 0.1 to about 10 mg/kg of body weight. In another embodiment, a dose of from about 0.1 to about 5 mg/kg, from about 0.1 to about 2.5 mg/kg body weight will be used. In other embodiments, the dose may be from about 1 to about 20 mg/kg of body weight or about 1 to about 10 mg/kg. In yet another embodiment, the dose may be from about 5 to about 20 mg/kg or about 10 to about 20 mg/kg of body weight.

In other embodiments for the treatment of livestock animals such as cattle or sheep, doses of the isoxazoline active agent administered may be about 0.1 to about 40 mg/kg of body weight. More typically the doses administered will be about 1 to about 30 mg/kg, about 1 to about 20 mg/kg or about 1 to about 10 mg/kg of body weight. In yet another embodiment, the dose may be from about 10 to about 25 mg/kg, about 15 to about 30 mg/kg of body weight or about 20-30 mg/kg of body weight.

In some embodiments, the dose of the isoxazoline active agent is the dose that is administered by the antiparasitic external devices of the present disclosure over 1, 2, or 3 months period of time.

In some embodiments, the dose of the isoxazoline active agent administered by the antiparasitic external devices of the present disclosure is the dose of isoxazoline delivered by the external device over 3 or more months, such as over at least 4, 5, 6, 7, 8, and 9 or more months.

In some embodiments, the dose of isoxazoline active agent administered over a period of time may be about 100, 200, 300, 400, or more than 500 mg/kg of an animal's body weight. In one embodiment, the dose is at least 550 mg/kg of body weight. In another embodiment, the dose is at least 600, 650, 700, 750, 800, 850, or 900 mg/kg of isoxazoline delivered relative to animal's body weight by the long acting antiparasitic external device over the period of time that the device is worn by an animal.

In one embodiment of the method of use in livestock animals (e.g., cattle or sheep), the long-acting antiparasitic external devices of the present disclosure comprising an isoxazoline compound has an efficacy against ectoparasites including, but not limited to, ticks, mites, lice and parasitic flies, of at least about 90.0% or higher for about 3 months, or longer. In another embodiment, the long-acting antiparasitic external devices of the present disclosure provide an efficacy against ectoparasites of at least 95.0% or higher for about 3 months or longer.

In another embodiment, the long-acting antiparasitic external devices of the present disclosure provide an efficacy against ectoparasites in livestock animals (e.g., cattle or sheep) of at least about 80% for two months, or longer. In another embodiment, the long-acting antiparasitic external devices of the present disclosure efficacy against ectoparasites in livestock animals (e.g., cattle or sheep) of about 90% for at least about 2 months. In still another embodiment, the antiparasitic external devices provide an efficacy of about 95% for about 2 months or longer. In another embodiment, the long-acting antiparasitic external devices of the present disclosure efficacy against ectoparasites in livestock animals (e.g., cattle or sheep) of about 90% for about 3 months, 6 month, 9 months, or longer. In still another embodiment, the antiparasitic external devices provide an efficacy of about 95% for about 3 months or longer. In still another embodiment, the antiparasitic external devices provide an efficacy of about 95% for about 6 months or longer. In another embodiment, the antiparasitic external devices provide an efficacy of about 95% for about 9 months or longer.

In another embodiment, the long-acting antiparasitic external devices of the present disclosure have an efficacy of at least about 80% against ectoparasites for about 3 months, or longer. In still another embodiment, the long-acting antiparasitic external devices of the present disclosure provide an efficacy of at least about 90% against ectoparasites for 3 months or longer. In yet another embodiment, the long-acting antiparasitic external devices of the present disclosure of the present disclosure provide an efficacy of at least about 95% against ectoparasites for 3 months or longer. In still another embodiment, the long-acting antiparasitic external devices of the present disclosure provide an efficacy against ectoparasites in livestock animals (e.g., cattle or sheep) of at least 80% or at least 90% for about 3 months to about 6 months or longer. In yet another embodiment, the long-acting antiparasitic external devices of the present disclosure provide an efficacy against ectoparasites in livestock animals (e.g., cattle or sheep) of at least 80% or at least 90% for about 9 months or longer.

EXAMPLES

The invention is further described by the following non-limiting examples which further illustrate the invention, and are not intended, nor should they be interpreted to, limit the scope of the invention.

Collars containing the isoxazoline active agents afoxolaner (Ia), esafoxolaner the active enantiomer of afoxolaner ((S)-Ia), and the active enantiomer of an analog having 3-chloro-4-fluoro-5-trifluoromethyl substitution on the phenyl ring (i.e. esafoxolaner modified to include a 4-fluoro group) ((S)-Id) as representative isoxazoline compounds were prepared with a variety of polymer matrices and evaluated for effectiveness to control ectoparasites on dogs.

Example 1

Preparation of Collars Containing Isoxazoline Active Agents

The conditions set forth in Table 1 below were used to produce collars for each given polymer. The extrusion was done using a Thermo Scientific HAAKE Minilab II microcompounder with conical twin-screws. The cycle time was sufficient to get thorough mixing of the active agent and polymer. The active agent loading was increased incrementally for a given polymer until the resulting collar became tacky to the touch and the active agent loading was kept below that threshold for testing. The extruder was cleaned out between samples to prevent cross contamination. The samples for both in vitro and the in vivo studies were made using identical methods except that the samples for the animal study were heated and stretched after extrusion to ensure the collar would be long enough to encircle a dog's neck comfortably.

As noted in Table 1, a higher loading of the isoxazoline active agents in PBS was possible compared with PVC, indicating a higher affinity of the active agents for PBS.

TABLE 1

Collar formulation and manufacturing parameters.

| Active agent loaded | Polymer matrix | Manufacturer | Polymer grade | Active agent loading | Temp. of extrusion | Cycle time | Screw Speed |
|---|---|---|---|---|---|---|---|
| (Ia) | Polyvinyl Chloride (PVC) | Roscom | 201-80 clear 01 | 11% | 165° C. | 3 min | 100 rotations per min |
| (S)-Id | Polyvinyl Chloride (PVC) | Roscom | 201-80 clear 01 | 11% | 165° C. | 3 min | 100 rotations per min |
| (S)-Ia | Polyvinyl Chloride (PVC) | Roscom | 201-80 clear 01 | 11% | 165° C. | 3 min | 100 rotations per min |
| (Ia) | Polybutylene succinate (PBS) | PTT MCC Biochem | FZ91 | 40% | 150° C. | 3 min | 100 rpm, slowed to 25 rpm for extrusion |
| (S)-Id | Polybutylene succinate (PBS) | PTT MCC Biochem | FZ91 | 40% | 150° C. | 3 min | 100 rpm, slowed to 25 rpm for extrusion |
| (S)-Ia | Polybutylene succinate (PBS) | PTT MCC Biochem | FZ91 | 40% | 150° C. | 3 min | 100 rpm, slowed to 25 rpm for extrusion |

Figure 2:
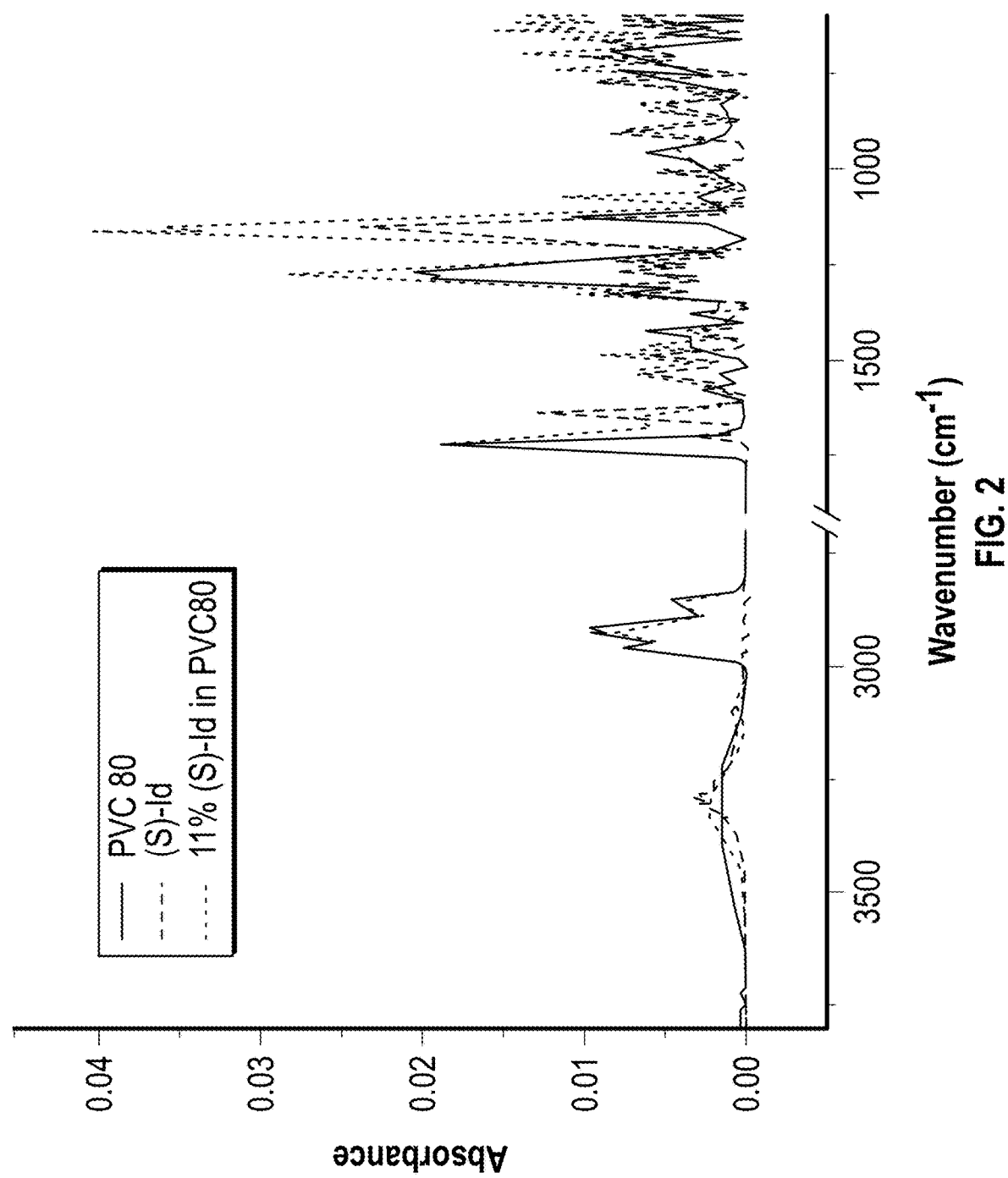
FIG. 2 ("Confirmation of (S)-Id in PVC matrix after extrusion and processing.") shows overlaying FTIR spectra of 1) a PVC80 matrix, 2) Compound (S)-Id, and 3) a PVC80 matrix containing 11% (w/w) of compound (S)-Id after extrusion and processing.
Figure 3:
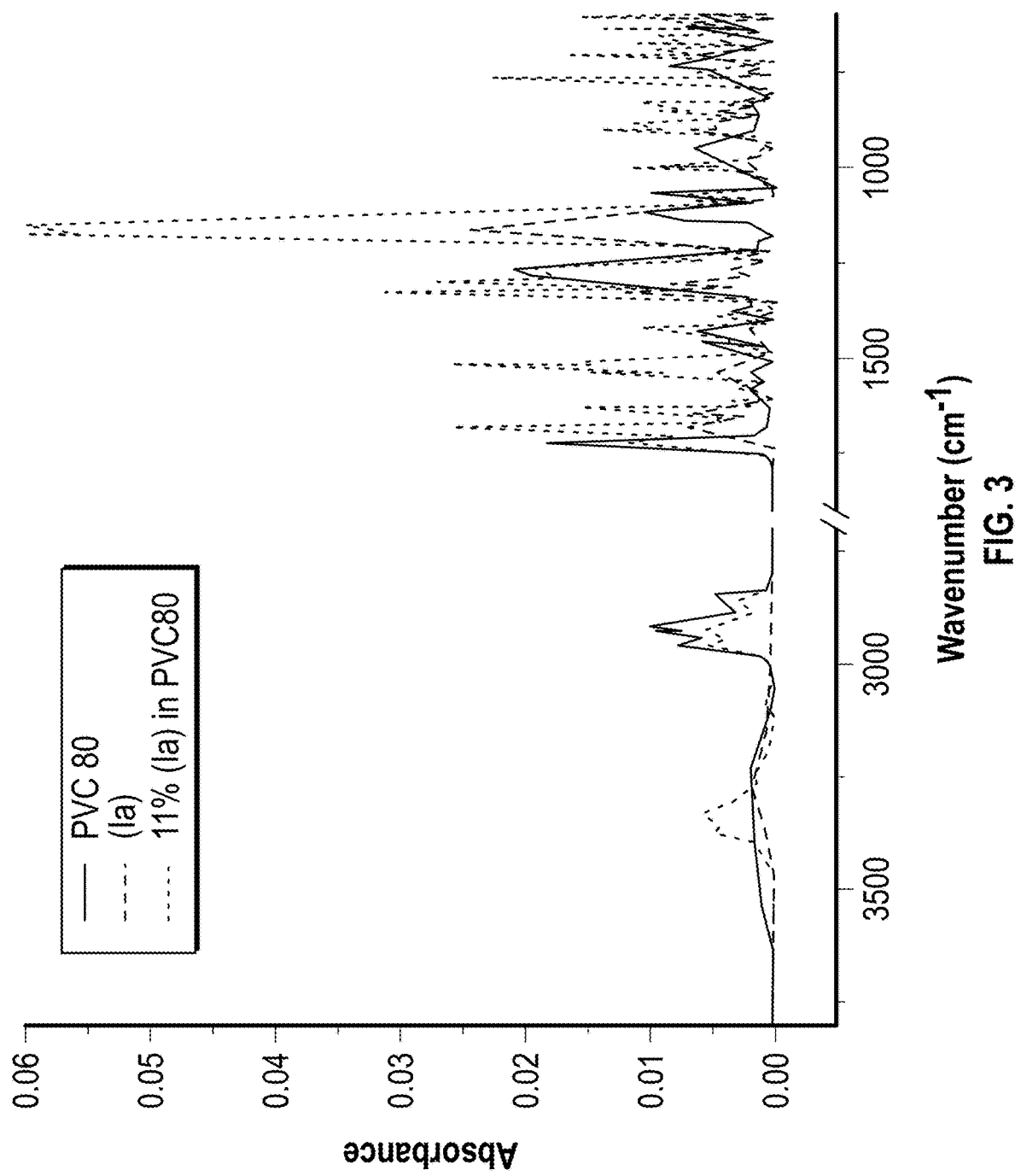
FIG. 3 ("Confirmation of (Ia) in PVC matrix after extrusion and processing.") shows overlaying FTIR spectra of 1) a PVC80 matrix, 2) Compound (Ia), and 3) a PVC80 matrix containing 11% (w/w) of compound (Ia) after extrusion and processing.

The presence of the active agent was confirmed using FTIR. Grazing angle ATR-FTIR was performed for the conformation of active agent within the polymer matrix after extrusion. A comparison of the polymer matrix used, PVC 80, and the different molecules yield peak differences at 1160 and 1640 cm$^{-1}$ as shown in FIG. 1-FIG. 3. The collar samples 11% (S)-Ia in PVC80, 11% (S)-Id in PVC80, and 11% Ia in PVC80 show overlap peaks for the characteristic isoxazoline active agent peaks, confirming the presence of the isoxazoline active agent, either (S)-Ia, (S)-Id, or Ia in the PVC matrix after extrusion and processing.

Figure 4:
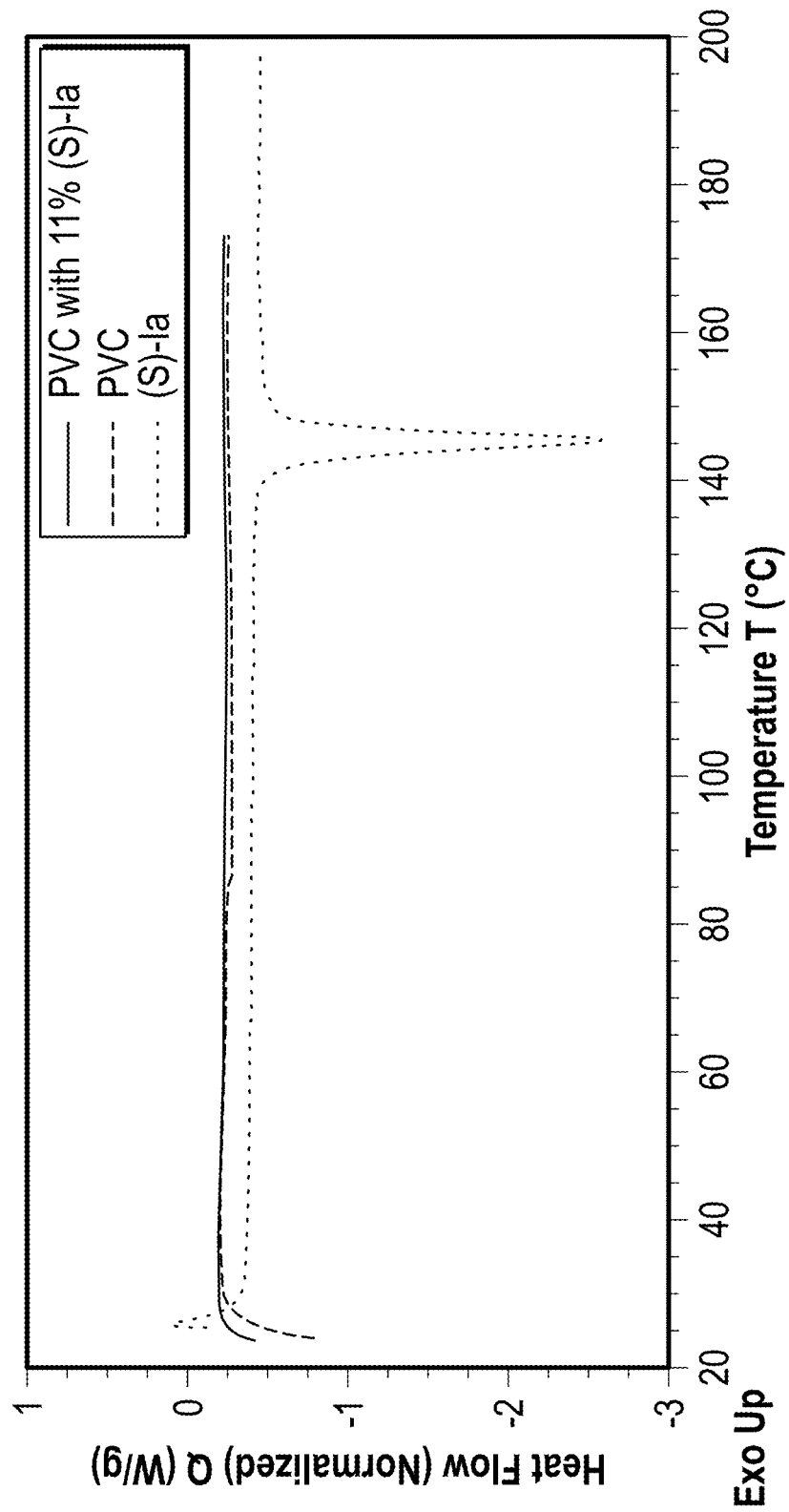
FIG. 4 shows differential scanning calorimetry ("DSC") curves of a PVC collar with compound (S)-Ia, PVC matrix, and compound (S)-Ia.

Differential Scanning calorimetry (DSC) was conducted on the above collars, along with the pure isoxazoline compounds and PVC matrix material. FIG. 4 is a comparison for (S)-Ia. The pure (S)-Ia has a distinctive melting peak around 145° C. After incorporating into the PVC matrix, the melting peak completely disappeared, resulting in a total amorphous dispersion of (S)-Ia in PVC. Similar phenomena were observed for PVC collars with isoxazoline compounds Ia and (S)-Id. Without wishing to be bound by theory, this transformation is believed to indicate that the drug can move relatively freely within the polymer matrix, and ultimately enable the drug to diffuse out of the collar and migrate into the dog's body.

The present disclosure is further described by the following non-limiting examples illustrating exemplary compositions of external parasitic collar compositions containing isoxazoline active agents:

| Formulation 1: | PVC | 50.0% (w/w) |
| | Stabilizer | 0.5% (w/w) |
| | Epoxidized soybean oil | 5.0% (w/w) |
| | Diisooctyl adipate | 34.5% (w/w) |
| | isoxazoline active agent | 10.0% (w/w) |
| Formulation 2: | PVC | 50.0% (w/w) |
| | Stabilizer | 0.5% (w/w) |
| | Epoxidized soybean oil | 5.0% (w/w) |
| | 2-Ethyl diphenyl phosphate | 30.0% (w/w) |
| | isoxazoline active agent | 14.5% (w/w) |
| Formulation 3: | PVC | 50.0% (w/w) |
| | Stabilizer | 0.5% (w/w) |
| | Epoxidized soybean oil | 5.0% (w/w) |
| | Diisooctyl adipate | 30.0% (w/w) |
| | Compound of formula (Ia) | 14.5% (w/w) |
| Formulation 4: | PVC | 50.0% (w/w) |
| | Stabilizer | 0.5% (w/w) |
| | Epoxidized soybean oil | 5.0% (w/w) |
| | 2-Ethyl diphenyl phosphate | 14.5% (w/w) |
| | Compound of formula (Ia) | 30.0% (w/w) |
| Formulation 5: | EPDM | 50.0% (w/w) |
| | Stabilizer | 0.5% (w/w) |
| | Epoxidized soybean oil | 5.0% (w/w) |
| | Diisooctyl adipate | 34.5% (w/w) |
| | isoxazoline active agent | 10.0% (w/w) |
| Formulation 6: | EPDM | 50.0% (w/w) |
| | Stabilizer | 0.5% (w/w) |
| | Epoxidized soybean oil | 5.0% (w/w) |
| | 2-Ethyl diphenyl phosphate | 30.0% (w/w) |
| | isoxazoline active agent | 14.5% (w/w) |
| Formulation 7: | EPDM | 50.0% (w/w) |
| | stearate | 0.5% (w/w) |
| | Epoxidized soybean oil | 5.0% (w/w) |
| | Diisooctyl adipate | 30.0% (w/w) |
| | Compound of formula (Ia) | 14.5% (w/w) |
| Formulation 8: | EPDM | 50.0% (w/w) |
| | Stearate | 0.5% (w/w) |
| | Epoxidized soybean oil | 5.0% (w/w) |
| | 2-Ethyl diphenyl phosphate | 14.5% (w/w) |
| | Compound of formula (Ia) | 30.0% (w/w) |
| Formulation 9: | PVC | 50.0% (w/w) |
| | Stearate | 0.5% (w/w) |
| | Epoxidized soybean oil | 5.0% (w/w) |
| | Diisooctyl adipate | 34.5% (w/w) |
| | isoxazoline active agent | 10.0% (w/w) |
| Formulation 10: | PVC | 50.0% (w/w) |
| | Stearate | 0.5% (w/w) |
| | Epoxidized soybean oil | 5.0% (w/w) |
| | 2-Ethyl diphenyl phosphate | 30.0% (w/w) |
| | isoxazoline active agent | 14.5% (w/w) |
| Formulation 11: | PVC | 50.0% (w/w) |
| | Epoxidized soybean oil | 5.0% (w/w) |
| | Diisooctyl adipate | 30.0% (w/w) |
| | Compound of formula(S)-Ia | 15.0% (w/w) |

-continued

| Formulation 12: | PVC | 50.0% (w/w) |
| --- | --- | --- |
| | Stabilizer | 0.5% (w/w) |
| | 2-Ethyl diphenyl phosphate | 19.5% (w/w) |
| | Compound of formula(S)-Ia | 30.0% (w/w) |
| Formulation 13: | EPDM | 50.0% (w/w) |
| | Stabilizer | 0.5% (w/w) |
| | Epoxidized soybean oil | 5.0% (w/w) |
| | Diisooctyl adipate | 34.5% (w/w) |
| | Compound of formula(S)-Ia | 10.0% (w/w) |
| Formulation 14: | EPDM | 50.0% (w/w) |
| | Stabilizer | 0.5% (w/w) |
| | Epoxidized soybean oil | 5.0% (w/w) |
| | 2-Ethyl diphenyl phosphate | 30.0% (w/w) |
| | Compound of formula(S)-Ia | 14.5% (w/w) |
| Formulation 15: | EPDM | 50.0% (w/w) |
| | Stabilizer | 0.5% (w/w) |
| | Epoxidized soybean oil | 5.0% (w/w) |
| | Diisooctyl adipate | 30.0% (w/w) |
| | Compound of formula Ic where $X^1$, $X^3$ = Cl, $X^2$ is F | 14.5% (w/w) |
| Formulation 16: | EPDM | 50.0% (w/w) |
| | Stabilizer | 0.5% (w/w) |
| | Epoxidized soybean oil | 5.0% (w/w) |
| | 2-Ethyl diphenyl phosphate | 14.5% (w/w) |
| | Compound of formula Ic where $X^1$, $X^3$ = Cl, $X^2$ is F | 30.0% (w/w) |
| Formulation 17: | PVC | 50.0% (w/w) |
| | Stabilizer | 0.5% (w/w) |
| | Epoxidized soybean oil | 5.0% (w/w) |
| | 2-Ethyl diphenyl phosphate | 14.5% (w/w) |
| | Compound of formula (Id) | 30.0% (w/w) |
| Formulation 18: | EPDM | 50.0% (w/w) |
| | Stabilizer | 0.5% (w/w) |
| | Epoxidized soybean oil | 5.0% (w/w) |
| | Diisooctyl adipate | 34.5% (w/w) |
| | Compound of formula (Id) | 10.0% (w/w) |
| Formulation 19: | PVC | 50.0% (w/w) |
| | Stabilizer | 0.5% (w/w) |
| | Epoxidized soybean oil | 5.0% (w/w) |
| | 2-Ethyl diphenyl phosphate | 14.5% (w/w) |
| | Compound of formula (Id) | 30.0% (w/w) |
| Formulation 20: | EPDM | 50.0% (w/w) |
| | Stabilizer | 0.5% (w/w) |
| | Epoxidized soybean oil | 5.0% (w/w) |
| | Diisooctyl adipate | 34.5% (w/w) |
| | Compound of formula (Id) | 10.0% (w/w) |

In addition, the collar formulations described in Table 2 comprising a polyvinyl chloride (PVC) matrix and afoxolaner were produced. The collars for each given formulation described in Table 2 were produced by extrusion or injection molding. The extrusion conditions were 155° C., 25 rpm screw speed, and no cycle. The injection mold conditions were 150° C. cylinder, 45° C. mold, and 600 psi for 5 seconds.

TABLE 2

PVC collar formulations.

| Afoxolaner, wt % | PVC, wt % | Bis(2-ethylhexyl) phthalate, wt % | Zinc Stearate, wt % | Acrawax, wt % |
| --- | --- | --- | --- | --- |
| 0 | 66.45 | 29.9 | 2.66 | 0.9 |
| 5 | 63.1 | 28.4 | 2.5 | 0.9 |
| 7 | 61.8 | 27.8 | 2.5 | 0.9 |
| 9 | 60.4 | 27.2 | 2.4 | 0.9 |
| 11 | 5931 | 26.7 | 2.3 | 0.9 |

Example 2

In Vitro Efficacy of Antiparasitic External Device Compositions Comprising Isoxazoline Active Agent Against Fleas (*Ctenocephalides felis*)

The in-vitro susceptibility of *Ctenocephalides felis* exposed to treated filter papers and to external device compositions (antiparasitic collar) containing isoxazoline active agents (S)-Ia, (S)-Id and (Ia) was determined, wherein the collars comprise a polyvinyl chloride (PVC) matrix or a polybutylene succinate (PBS) matrix.

TABLE 3

Test groups for in-vitro flea exposure effectiveness.

| Trt. No. | Investigational Material | Active Agent loading | Treatment Day | No. of Replicated Vials of 20 Fleas Each |
| --- | --- | --- | --- | --- |
| 1 | Untreated Control PVC Collar | NA | Day 0 | 3 |
| 2 | Untreated Control PBS Collar | NA | Day 0 | 3 |
| 3 | PVC + (S)-Ia | 11% | Day 0 | 3 |
| 4 | PBS + (S)-Ia | 40% | Day 0 | 3 |
| 5 | PVC + (S)-Id | 11% | Day 0 | 3 |
| 6 | PBS + (S)-Id | 40% | Day 0 | 3 |
| 7 | PVC + (Ia) | 11% | Day 0 | 3 |
| 8 | PBS + (Ia) | 40% | Day 0 | 3 |
| 9 | Acetone Only Control on Filter Paper | NA | Day 0 | 3 |
| 10 | (S)-Ia on Filter Paper | 10 mg/mL | Day 0 | 3 |
| 11 | (S)-Ie on Filter Paper | 10 mg/mL | Day 0 | 3 |
| 12 | (Ia) on Filter Paper | 10 mg/mL | Day 0 | 3 |

To determine the in-vitro susceptibility of *Ctenocephalides felis* exposed to treated filter papers or to the collars compositions comprising the isoxazoline active agent, approximately 20 fleas were transferred to vials containing either the collars or filter papers in accordance with the test groups outlined in Table 3. On Day 0, approximately 20 fleas were placed in 27×55 mm, 5 dram glass vials containing the collars comprising the active agent as outlined in Table 3 or in 60 mm×40 mm glass vials containing treated filter papers. The filter papers tested in groups 9-12 were loaded with 500 μL of a 10 mg/mL solution containing the active agent dissolved in acetone. Each strip of collar was 10 cm in length and each filter paper had an area of 21 cm². Test vials were placed in an environmental chamber at approximately 28° C. and approximately 80% RH.

The number of dead fleas in each vial were counted on Day 1 at 24 (±1) hours after initial exposure. Fleas were counted as dead if they were not able to maintain an upright posture. The In-vitro flea exposure effectiveness of the various test groups outlined in Table 3 is summarized in Table 4.

TABLE 4

In-vitro flea exposure effectiveness results.

| Trt. No. | Vial 1 # Live Fleas | Vial 2 # Live Fleas | Vial 3 # Live Fleas | Geometric Mean No. Live Fleas | Percentage Reduction Live Fleas |
| --- | --- | --- | --- | --- | --- |
| 1 (Control PVC) | 19 | 19 | 21 | 19.6 | N/A |
| 2 (Control PBS) | 20 | 20 | 20 | 20.0 | N/A |

TABLE 4-continued

In-vitro flea exposure effectiveness results.

| Trt. No. | Vial 1 # Live Fleas | Vial 2 # Live Fleas | Vial 3 # Live Fleas | Geometric Mean No. Live Fleas | Percentage Reduction Live Fleas |
|---|---|---|---|---|---|
| 3 PVC + (S)-Ia | 0 | 0 | 0 | 0 | 100% |
| 4 PBS + (S)-Ia | 20 | 20 | 19 | 19.7 | 1.7% |
| 5 PVC + (S)-Id | 2 | 0 | 0 | 0.4 | 99.6% |
| 6 PBS + (S)-Id | 19 | 18 | 20 | 19.0 | 5.1% |
| 7 PVC + (Ia) | 1 | 2 | 1 | 1.3 | 98.7% |
| 8 PBS + (Ia) | 18 | 18 | 20 | 18.6 | 6.8% |
| 9 (Control Filter Paper) | 19 | 21 | 21 | 20.3 | N/A |
| 10 (S)-Ia on Filter Paper | 19 | 20 | 18 | 19.0 | 6.5% |
| 11 (S)-Ie on Filter Paper | 19 | 20 | 15 | 12.0 | 12.0% |
| 12 (Ia) on Filter Paper | 19 | 21 | 19 | 19.6 | 3.3% |

These study data demonstrate that antiparasitic collar compositions comprising an isoxazoline active agent formulated in PVC effectively kill fleas in contact with the collar material. In contrast, groups containing collar strips produced from PBS and filter papers containing the isoxazoline compounds did not have an impact on the fleas in the in vitro contact assay.

Example 3

In Vivo Efficacy of PVC Collar Compositions Comprising Isoxazoline Active Agent Against Fleas (*Ctenocephalides felis*) and Ticks (*Rhipicephalus sanguineus*) on Dogs Twenty four dogs were studied to determine the effectiveness of a collar comprising an isoxazoline active agent formulated in a PVC matrix against induced infestations of *Ctenocephalides felis* and *Rhipicephalus sanguineus*.

Prior to treatment application dogs were infested with approximately 100 *C. felis* (i.e. prior to collar application) on Day-5, and randomized to a treatment group based on their flea counts determined at 48 (±2) hours after infestation.

Four Treatment Groups each containing six dogs were formed. Dogs in Group 1 were untreated (a blank collar was applied which did not contain an isoxazoline active). Dogs in Groups 2, 3 and 4 were treated with the collar composition described in Table 5. All dogs were treated once on Day 0 (i.e. the collars were fitted on the dogs on Day 0).

Dogs were re-infested with approximately 100 *C. felis* post collar application on Days 4, 12, 27, 41, 89 and 109. Flea counts were done 48 hours after infestation with the exception of the Day 89 and 109 infestation which was evaluated at 24 hours after infestation.

All dogs were also infested with either approximately 50 *R. sanguineus* on Days 19 and 55 or with approximately 50 *D. variabilis* on Day 67. Ticks were counted 72 hours after the infestation carried out on Day 19 and 48 hours after the infestations carried out on Days 55 and 67.

Flea efficacy is listed in Table 6 and tick efficacy is listed in Table 7 below.

Percent reduction (also referred as efficacy based on Arithmetic Mean flea counts for each treatment group in comparison to the untreated group) against fleas was at least 89% through and including Day 166 for all treatment groups (see Table 6).

The percent reduction against ticks was at least 58% through and including Day 153 (see Table 7) for all treatment groups.

These study data demonstrate that parasitic collar compositions comprising an isoxazoline active agent provide excellent efficacy against fleas and ticks on dogs.

TABLE 5

Test groups for in-vivo flea and tick exposure effectiveness of collar compositions.

| Trt. No. | Investigational Material | Active Agent loading | Route | Trt. Day | Total number of Animals |
|---|---|---|---|---|---|
| 1 | Blank Control (PVC only) | NA | Neck Collar | 0 | 6 |
| 2 | PVC Collar + (Ia) | 11% | Neck Collar | 0 | 6 |
| 3 | PVC Collar + (S)-Ia | 11% | Neck Collar | 0 | 6 |
| 4 | PVC Collar + (S)-Id | 11% | Neck Collar | 0 | 6 |

TABLE 6

Flea Efficacy of collar application.

| | % Reduction Fleas | | | | | | | |
|---|---|---|---|---|---|---|---|---|
| Trt. No. | Day 6 | Day 14 | Day 29 | Day 43 | Day 90 | Day 110 | Day 138 | Day 166 |
| Group 2 | | | | | | | | |
| % Reduction | 100.0 | 100.0 | 100.0 | 100.0 | 94.8 | 92.2 | 91.5 | 88.9 |
| Group 3 | | | | | | | | |
| % Reduction | 100.0 | 99.7 | 100.0 | 100.0 | 99.6 | 100 | 98.9 | 100.0 |
| Group 4 | | | | | | | | |
| % Reduction | 100.0 | 100.0 | 100.0 | 100.0 | 98.7 | 97.7 | 97.2 | 90.6 |

TABLE 7

Tick Efficacy of collar application.

| Trt. No. | % Reduction Ticks | | | | |
|---|---|---|---|---|---|
| | Day 22 | Day 57 | Day 69 | Day 125 | Day 153 |
| Group 2 | | | | | |
| % Reduction | 100.0 | 100.0 | 91.3 | 81.3 | 74.6 |
| Group 3 | | | | | |
| % Reduction | 100.0 | 100.0 | 99.2 | 93.6 | 82.5 |
| Group 4 | | | | | |
| % Reduction | 100.0 | 100.0 | 94.3 | 91.8 | 57.7 |

PK data: Blood samples from all the dogs were taken periodically and drug concentrations in the plasma were analyzed (depicted in FIG. 5). As indicated, significant amounts of all three isoxazoline compounds were present in the dog blood, suggesting that these isoxazoline compounds trandermally permeated through the dog skin and into the blood stream. In other words, these compounds are likely acting by a systemic mechanism, even though they are applied in a topical collar dosage form. These PK data appear also to correlate with the flea and tick efficacy data in Table 6 and 7 (e.g., compound (S)-Ia is the best, (S)-Id is the second, and Ia the third).

Figure 6:
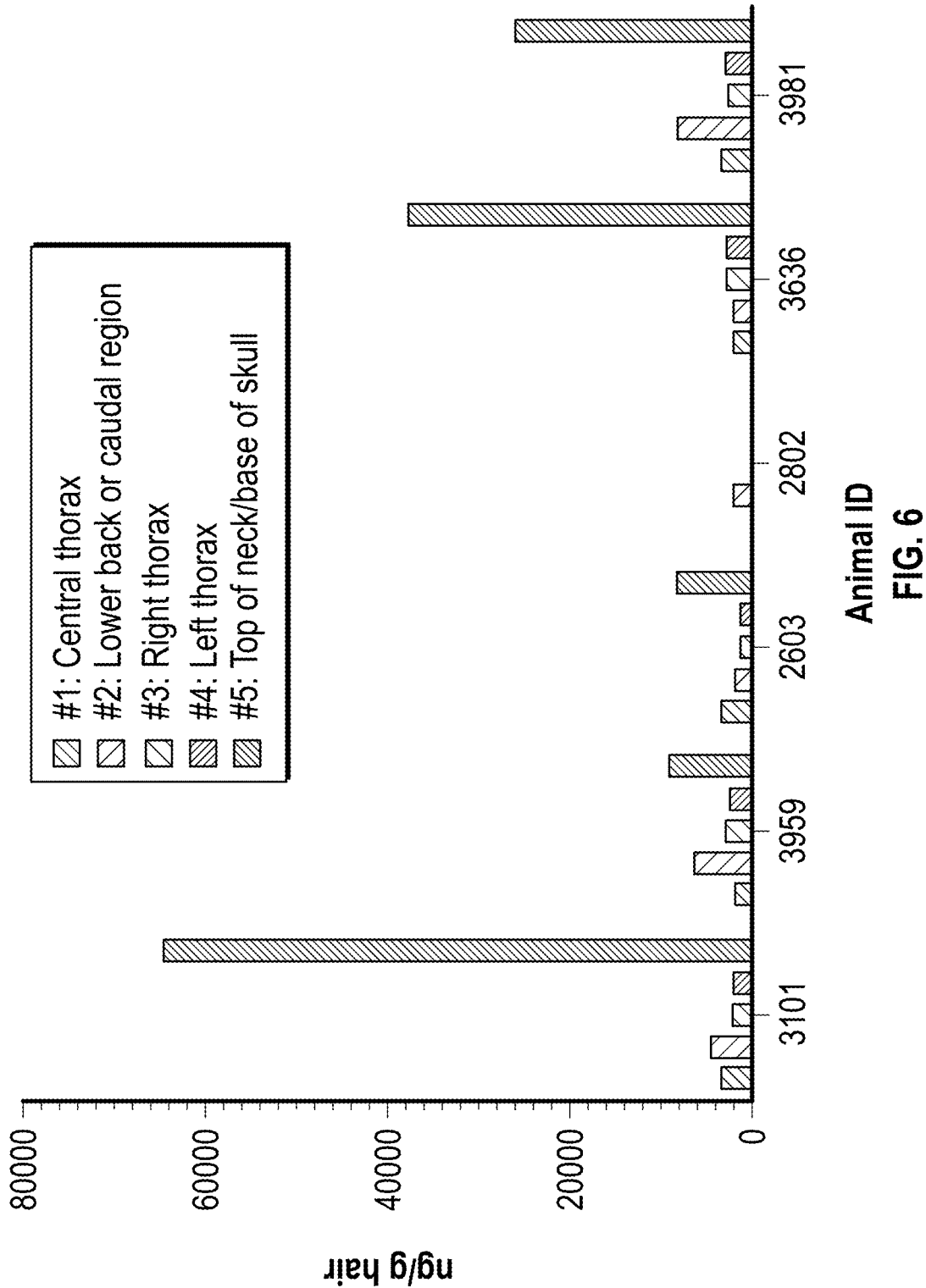
FIG. 6 shows drug concentrations in hairs of different parts of the dogs after wearing compound (S)-Id containing collars for 166 days (comparing drug concentration in central thorax, lower back or caudal region, right thorax, left thorax, and top of neck/base of skull).

Isoxazoline Compounds in Dog Hair:

Hair samples from each dog were collected on Day 110 from 5 different areas: (1) central thorax, (2) lower back/caudal region, (3) right thorax, (4) left thorax, and (5) top of neck/base of skull above collar site. Suitable bioanalytical methods were used for analysis of the three isoxazoline compounds in dog hair. FIG. 6 shows the results for (S)-Id. Overwhelmingly the "top of the neck" where the PVC/isoxazoline collars were located had the highest level of the drug, even though there were detectable isoxazoline compound levels throughout bodies of the dogs. Results for the other two isoxazoline compounds Ia and (S)-Ia are very similar. This pattern suggests that the isoxazoline compounds first migrated from the collars to the dog hairs, then permeated through the skin to the blood stream.

Example 4

Collars with Other Polymer Matrices

Several new polymers were evaluated for making collars with isoxazoline compounds including polybutylene succinate (PBS), polybutylene succinate adipate (PBSA), ethylene vinyl acetate copolymer (EVA), polycaprolactone (PCL), and polylactide (PLA). To soften the rigidity of some polymers, triethyl citrate (TEC) was used as a plasticizer. Table 8 is a summary of the collar formulations with compound (S)-Ia as a model isoxazoline compound.

All polymer resins were cryomilled to a fine powder and then mixed with compound (S)-Ia individually. Samples were made up in 600 g batches with target 11 wt % active loading in each batch. All mixtures were hand mixed with a spatula to insure uniformity in the formulation. The formulations are shown in Table 8. Collars were formed in a Leistritz 18 mm twin-screw extruder under the process parameters listed in Table 9. Buckles were manually attached post extrusion for PK (i.e. pharmacokinetic) studies.

TABLE 8

Formulations of experimental collars with non-PVC polymers

| Polymer, wt % | Manufacturer | Grade | TEC, wt % | Active (S-Ia), wt % |
|---|---|---|---|---|
| EVA | Celanese | 12% VA | — | 11 |
| PBS | MCC Biochem | FZ91 | — | 11 (feeding) |
| PBS | MCC Biochem | FZ91 | 10 | 10 (actual) |
| PB SA | MCC Biochem | FD92 | — | 9 (actual) |
| PCL | Ingevity | 6500D | 20 | 11 (feeding) |
| PLA | Natureworks | 4060D | 10 | 11 (feeding) |

TABLE 9

Extrusion conditions of collars with various polymers

| Matrix | Screw speed (RPM) | Temperature (° C.) | | | | | | |
|---|---|---|---|---|---|---|---|---|
| | | Zone 1 | Zone 2 | Zone 3 | Zone 4 | Zone 5 | Zone 6 | Zone 7 |
| EVA | 50 | 180 | 180 | 180 | 170 | 150 | 150 | 150 |
| PBS | 50 | 155 | 155 | 145 | 125 | 125 | 125 | 125 |
| PBS + 10% TEC | 50 | 155 | 155 | 145 | 125 | 125 | 125 | 125 |
| PBSA | 50 | 150 | 150 | 115 | 115 | 95 | 84 | 78 |
| PCL + 20% TEC | 50 | 155 | 155 | 145 | 100 | 85 | 85 | 70 |
| PLA + 10% TEC | 50 | 180 | 180 | 180 | 180 | 180 | 175 | 140 |

DSC Test

Figure 7:
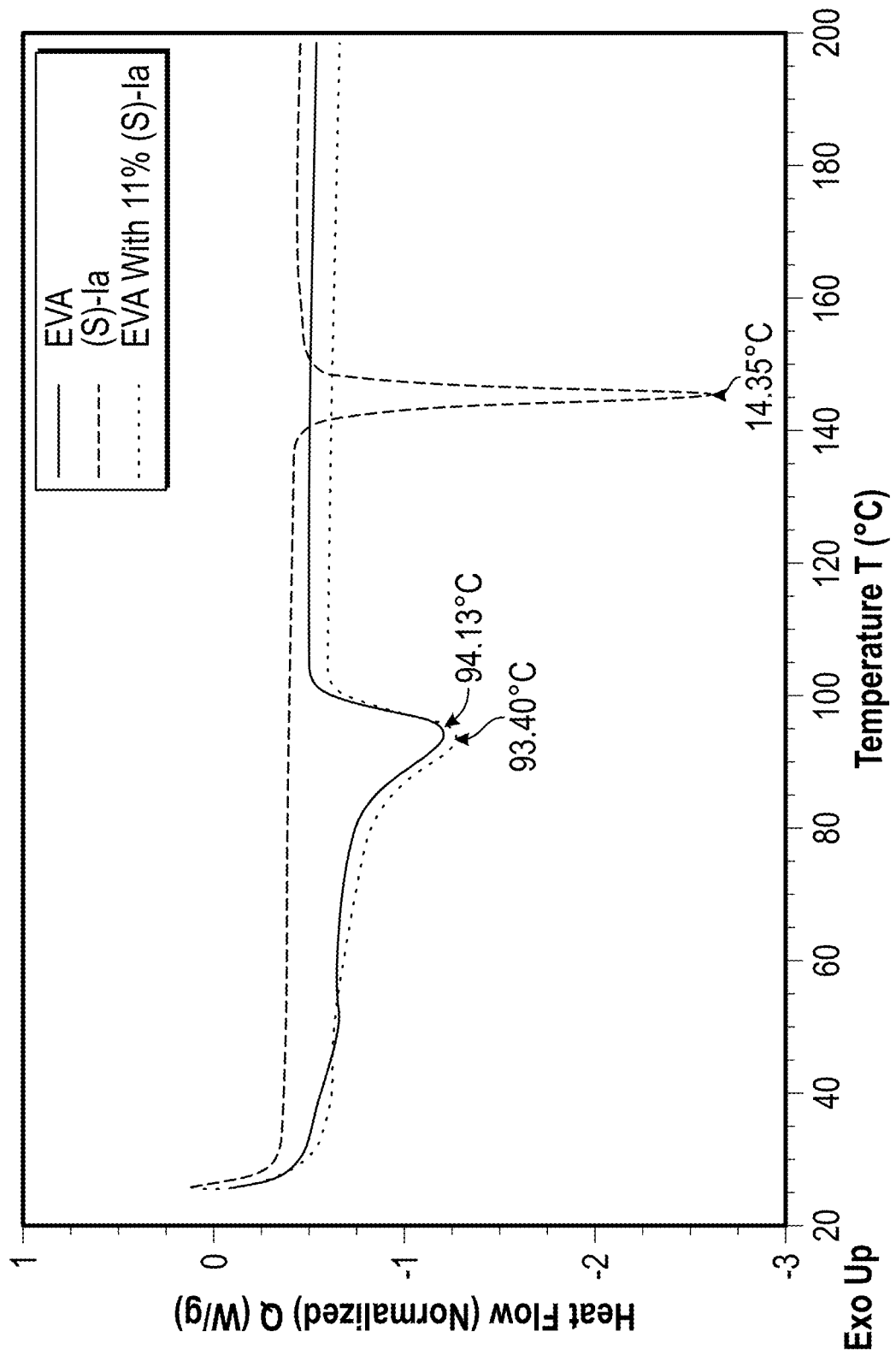
FIG. 7 shows DSC curves of an EVA collar with compound (S)-Ia, EVA matrix, and compound (S)-Ia.
Figure 8:
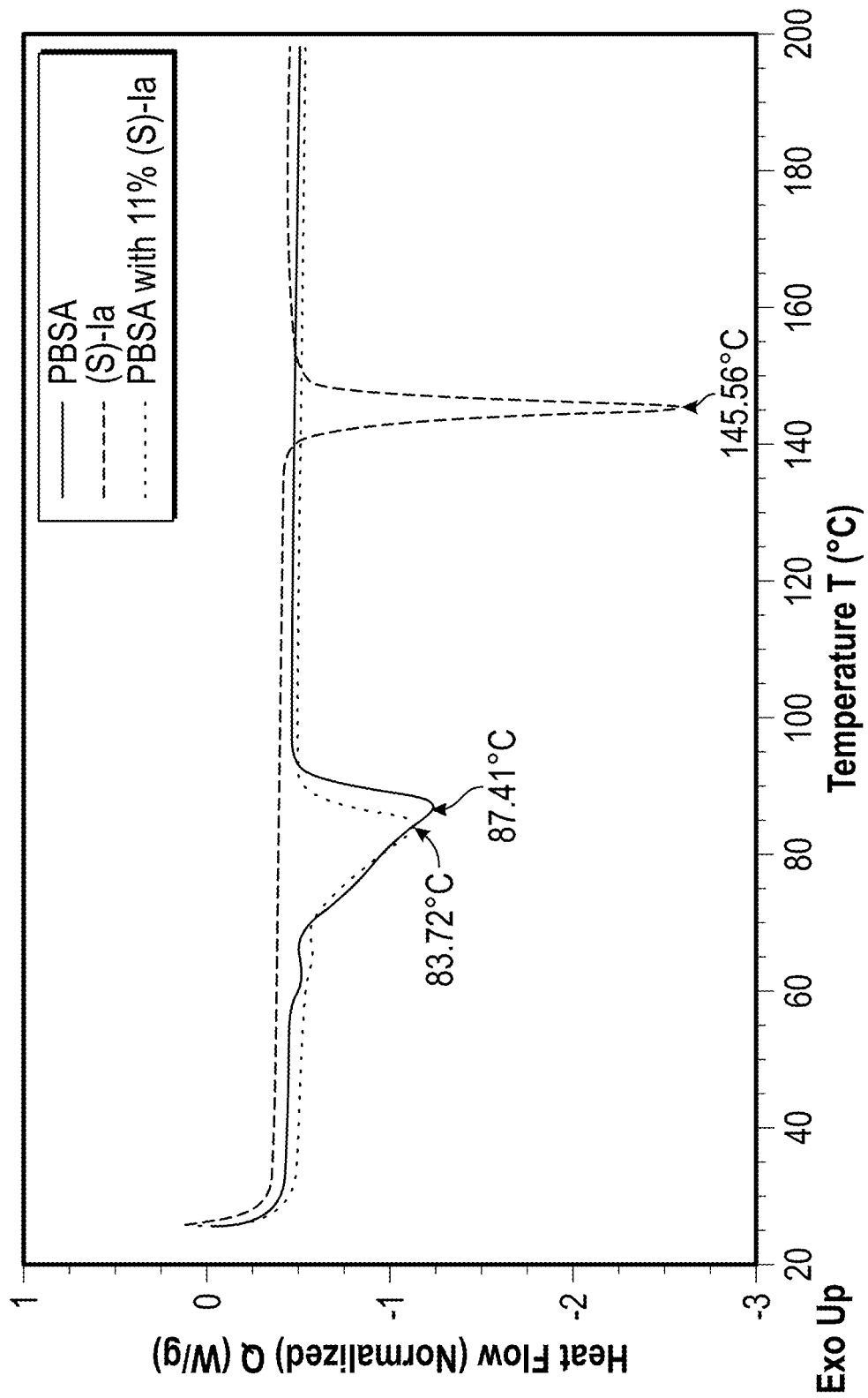
FIG. 8 shows DSC curves of a PBSA collar with compound (S)-Ia, PB SA matrix, and compound (S)-Ia.

The resulting collars were analyzed on DSC, along with the isoxazoline compound (S)-Ia and corresponding polymers. FIG. 7 is the comparison for the EVA based collar and FIG. 8 for the PB SA based collar. As shown in FIG. 7 and FIG. 8, compound (S)-Ia became completely amorphous in the collars. It also plasticized both EVA and PB SA by depressing their melting points.

Mechanical Properties of Collars

For each polymer and sample type, 7-8 grams of polymer resin material was added to a HAAKE MiniLab II Twin Screw Extruder (Waltham Mass., USA), equipped with PolySoft OS and PolySoft Monitor Software. The extruder was equilibrated at the desired temperature before adding material, and the material was cycled before being loaded into the barrel of a HAAKE MiniJet Injection Molding Unit. Two ASTM type V dog bones were injection molded for each sample set.

Extruded 'dog bone' samples were tested with a Shimadzu Autograph AGS-X tensile tester (Kyoto, Japan), equipped with a 1 kN load cell and pneumatic clamps. Samples were pulled at a rate of 10 mm/minute and data was recorded until the sample broke. Tensile testing was conducted in duplicate to establish a rough standard deviation. The equipped TRAPEZIUMX software was used to calculate Young's Modulus, strain at break, yield strength (if present), and stress at break.

TABLE 10

Hand feel and dimensions of the experimental collars

| Rank | Matrix | Hand feel | Dimensions, mm | |
| | | | Width | Thickness |
|---|---|---|---|---|
| 1 | EVA (12% VA) | Soft, flexible, yet strong. Feels very good | 13.0 | 1.8 |
| 2 | PVC (round 1) | Soft, flexible, good strength. Feels good | 3.8 | 1.4 |
| 3 | PBSA | Very strong but slightly too rigid | 9.6 | 4.3 |
| 4 | PBS + 10% TEC | Very strong. Slightly too rigid but still easily bendable | 9.0 | 3.0 |
| 5 | PBS | Very strong but very rigid (though still bendable) | 8.5 | 3.8 |
| 6 | PLA + 10% TEC | Strong but too brittle (incompatibility). Easily broke when bent hard | 6.4 | 3.3 |
| 7 | PCL + 20% TEC | Did not form collars. Molten extrudate hardened too slowly | — | — |

TABLE 11

Mechanical properties of selected experimental collars

| Collar Matrix | Tensile Strength (Stress at Break, MPa) | Stiffness (Young's Modulus, MPa) | Elongation (Strain at Break, %) |
|---|---|---|---|
| Leading commercial collar (reference) | 5 | 5 | 178 |
| EVA | 6 | 15 | 241 |
| PVC | 8 | 71 | 109 |
| PBSA | 21 | 160 | 452 |
| PBS + 10% TEC | 35 | 247 | 232 |
| PBS | 37 | 361 | 199 |

Pharmacokinetics (PK) Study:

Thirty healthy Beagle dogs, 10 female and 20 male, with body weights from 7.85 to 16.87 kg (mean 11.93 kg) and ages of 8.3-94.0 months (mean: 46.4) were divided into five treatment groups with six dogs in each group. Experimental neck collars were applied to all the dogs on study day 0. Blood samples were collected at 1, 4, 7, 14, 21, 28, 35, and 42 days post collar application. The pre-dose blood samples were collected on Day-7. No dog lost the collar during the study.

Figure 5:
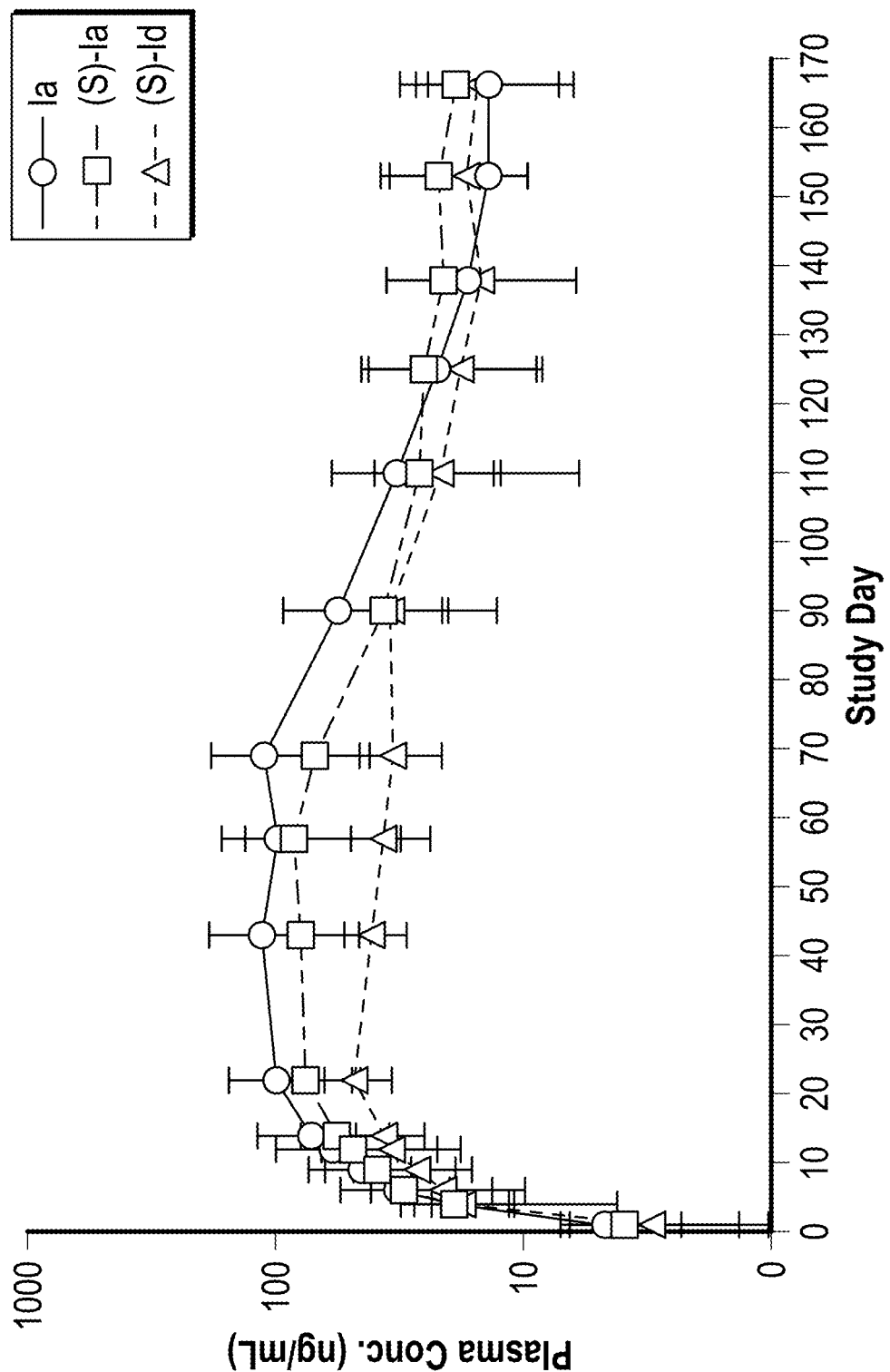
FIG. 5 shows plasma drug concentrations for dogs wearing PVC based isoxazoline collars (containing compounds (Ia), (S)-Ia, and (S)-Id)).
Figure 9:
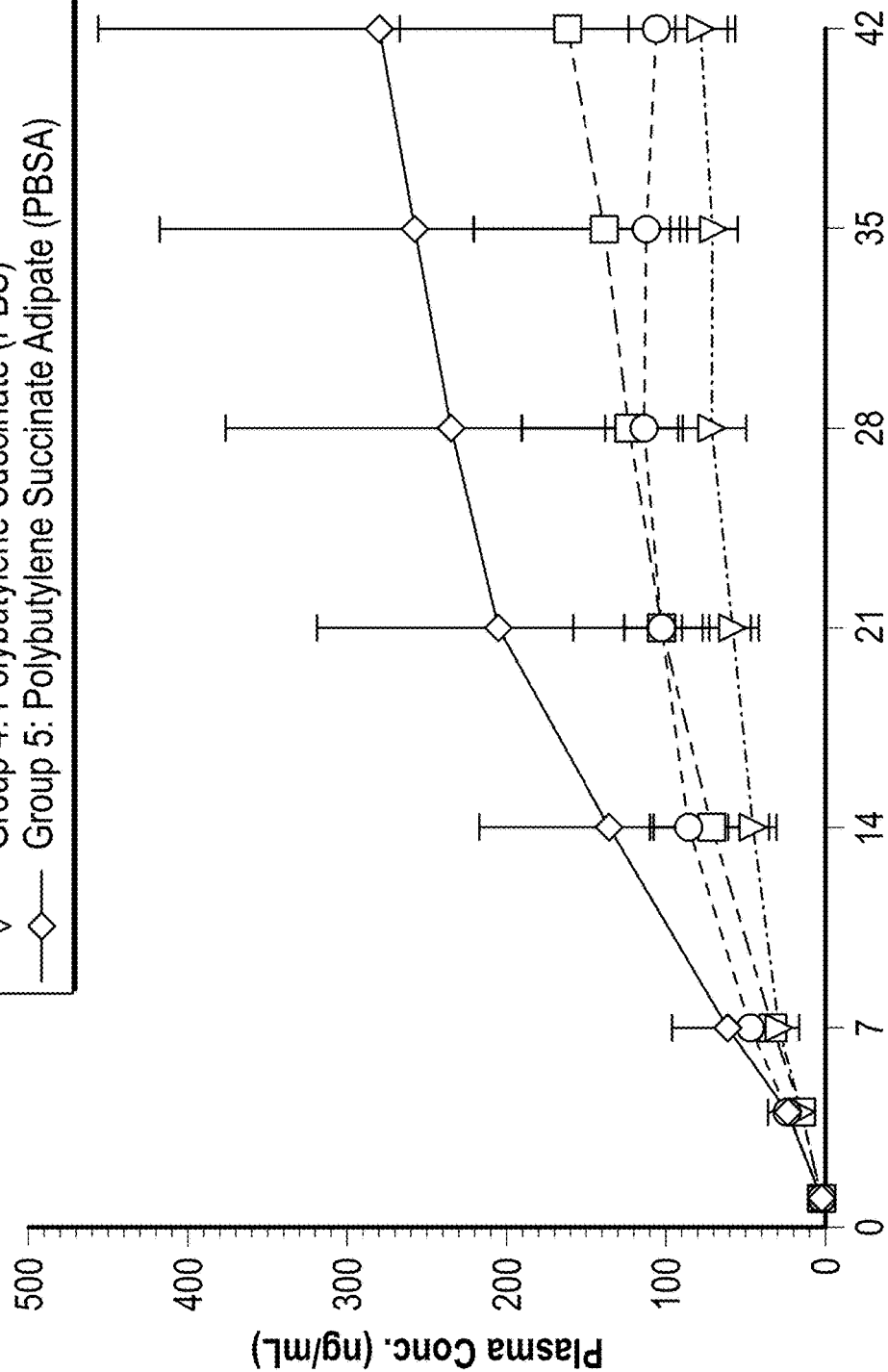
FIG. 9 shows pharmacokinetic ("PK") data of dogs after wearing collars with various non-PVC polymers including isoxazoline compound (S)-Ia.

FIG. 9 shows the PK profiles of the four groups with EVA, PBS, PBS/TEC, and PBSA collars each containing compound (S)-Ia. The Cmax of all four groups are between 50 and 300 ng/mL, similar to the PK study with the PVC collars (FIG. 5). Thus, the collars with EVA, PBS, PBS/TEC, and PBSA can be expected to have similar efficacy against fleas and ticks as the PVC collars.

The invention is further described by the following numbered paragraphs:

1. An antiparasitic external device for the treatment and/or prevention of a parasitic infection or infestation in an animal comprising:
  i) an effective amount of an isoxazoline active agent of formula (I):

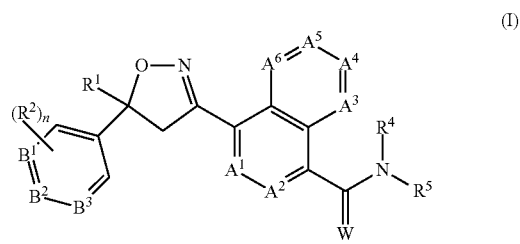

wherein:
$A_1$, $A^2$, $A^3$, $A^4$, $A^5$ and $A^6$ are independently selected from the group consisting of $CR^3$ and N, provided that at most 3 of $A_1$, $A^2$, $A^3$, $A^4$, $A^5$ and $A^6$ are N;
$B^1$, $B^2$ and $B^3$ are independently selected from the group consisting of $CR^2$ and N;
W is O or S;
$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;
each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN, —$SF_5$ or —$NO_2$;
each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$SF_5$ or —$NO_2$;
$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or
$R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;
each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;
each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;
each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN, —$SF_5$ or —$NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$SF_5$, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1, 2 or 3; or a pharmaceutically acceptable salt thereof; and ii) a polymer matrix.

2. The antiparasitic external device of paragraph 1, wherein: $R^1$ is $C_1$-$C_3$haloalkyl.

3. The antiparasitic external device of paragraph 1 or 2, wherein: $B^1$, $B^2$ and $B^3$ are independently $CR^2$; and $R^2$ is hydrogen, halogen or $C_1$-$C_3$haloalkyl.

4. The antiparasitic external device of any one of paragraphs 1 to 3, wherein: $A^1$, $A^2$, $A^3$, $A^4$, $A^5$ and $A^6$ are each independently $CR^3$; and $R^3$ is hydrogen, halogen, $C_1$-$C_3$alkyl or $C_1$-$C_3$haloalkyl.

5. The antiparasitic external device of any one of paragraphs 1 to 4, wherein $R^4$ is hydrogen, $C_1$-$C_3$alkyl or $C_1$-$C_3$haloalkyl.

6. The antiparasitic external device of any one of paragraphs 1 to 5, wherein: $R^5$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$.

7. The antiparasitic external device of paragraph 6, wherein: $R^7$ is halogen, $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl or $C_3$-$C_9$ dihaloalkylaminocarbonyl.

8. The antiparasitic external device of paragraph 7, wherein: $R^7$ is $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl or $C_3$-$C_9$ dihaloalkylaminocarbonyl.

9. The antiparasitic external device of any one of paragraph 1 to 8, wherein the compound of formula (I) has the formula (Ia) or (Id):

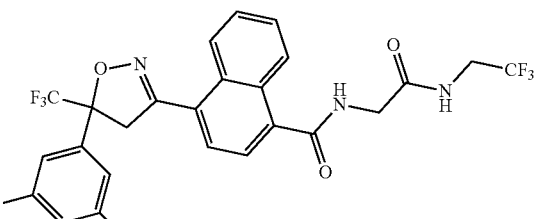

(Ia)

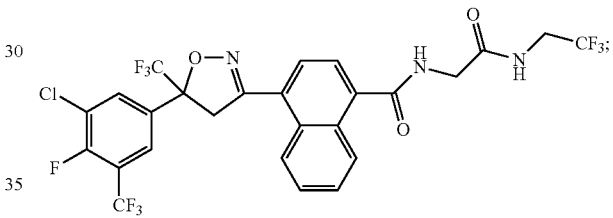

(Id)

10. The antiparasitic external device of any one of paragraphs 1 to 8, wherein the compound of formula (I) has the formula (S)-Ia or (S)-Id:

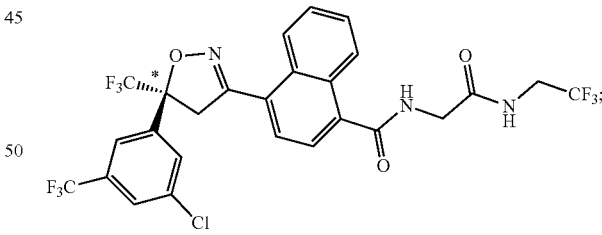

(S)-Ia

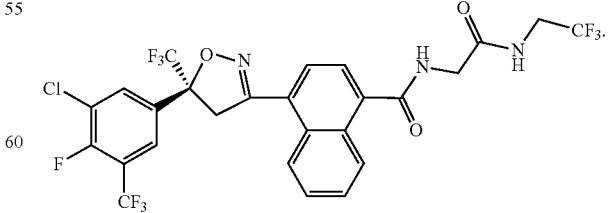

(S)-Id

11. The antiparasitic external device of any one of paragraphs 1 to 10, wherein the compound of formula (I) is present in a concentration of about 1 to about 40% (w/w).

12. An antiparasitic external device for the treatment and/or prevention of a parasitic infestation or infection in an animal comprising:
  i) an effective amount of at least one parasiticidal active agent, which is:
    a) a compound of formula (VII):

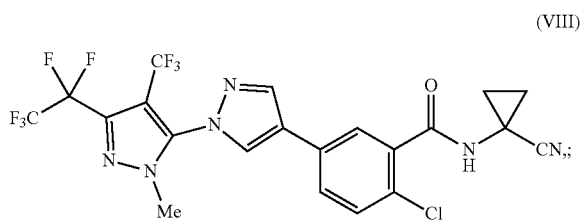 [SMILES: Cn1nc(C(F)(F)C(F)(F)F)c(C(F)(F)F)c1-n1cc(-c2ccc(Cl)c(C(=O)NC3(C#N)CC3)c2)cn1]

(VIII)

and/or
    b) a pharmaceutically acceptable salt or derivative of a compound of formula (VII); and
  ii) a polymer matrix.

13. The antiparasitic external device according to any one of paragraphs 1 to 12, wherein the polymer matrix comprises at least one polymer that is a vinyl polymer, a polyester, a nylon, a polyacrylate, a cellulosic polymer, or a thermoplastic polyurethane.

14. The antiparasitic external device according to paragraph 13 wherein the vinyl polymer comprises polyvinyl chloride (PVC), polyvinylidene chloride (PVDC), polyvinylidene fluoride (PVDF), polyethylene (PE), polypropylene (PP), chlorinated polyethylene (CPE), chlorinated polypropylene (CPP), ethylene-propylene copolymers, polyvinyl acetate (PVAc), ethylene-vinyl acetate copolymer (EVA), polyvinyl chloride-vinyl acetate, polyvinyl fluoride, polystyrene, polyisobutylene (PIB), styrene-butadiene rubber (SBR), styrene-isoprene rubber (SIS), or a combination thereof.

15. The antiparasitic external device according to paragraph 13 wherein the polyester comprises polyethylene terephthalate (PET), a PET copolymer, a polylactide (PLA), a PLA copolymer, polylactide-co-glycolide (PLGA), polycaprolactone (PCL), a PCL copolymer, a polyhydroxyalkanoate (PHA), polybutylene succinate (PBS), a polybutylene succinate-co-adipate (PB SA), a polybutylene adipate terephthalate (PBAT), or a combination thereof.

16. The antiparasitic external device according to paragraph 13, wherein the polymer matrix comprises a biodegradable polyester selected from polybutylene succinate (PBS); polybutylene succinate-co-adipate (PB SA); polylactide (PLA) and/or copolymers; polylactide-co-glycolide) (PLGA); polycaprolactone (PCL), PCL copolymer, a polyhydroxyalkanoate (PHA), a polybutylene adipate terephthalate (PBAT), or combinations thereof.

17. The antiparasitic external device according to paragraph 16, wherein the polymer matrix comprises a biodegradable polyester that is polybutylene succinate-co-adipate (PBSA) and/or polybutylene succinate (PBS) and/or polybutylene adipate terephthalate (PBAT).

18. The antiparasitic external device according to paragraph 13 wherein the polymer matrix comprises a nylon selected from the group consisting of Nylon 6, Nylon 66, and Nylon 12.

19. The antiparasitic external device according to paragraph 13 wherein the polymer matrix comprises at least one polyacrylate selected from the group consisting of polymethyl methacrylate (PMMA), polymethyl acylate (PMA), polyethyl methacrylate (PEMA), polybutyl methacrylate (PBMA), and their copolymers.

20. The antiparasitic external device according to paragraph 13, wherein the cellulosic polymer is cellulose acetate (CA) and/or ethylcellulose (EC).

21. The antiparasitic external device according to paragraph 13, wherein the polymer matrix comprises any one of polyvinyl acetate (PVAc), ethylene-vinyl acetate copolymer (EVA), polyvinyl chloride-vinyl acetate, or a mixture thereof.

22. The antiparasitic device according to paragraph 21, wherein the polymer matrix comprises ethylene-vinyl acetate copolymer (EVA).

23. The antiparasitic external device of any one of paragraphs 1 to 22, wherein the external device further comprises a plasticizer; optionally, a stabilizer, and optionally, an antioxidant.

24. An antiparasitic external device for the treatment and/or prevention of a parasitic infestation or infection in an animal comprising:
  i) an effective amount of at least one parasiticidal active agent, which is a compound of formula (Ia) or (Id):

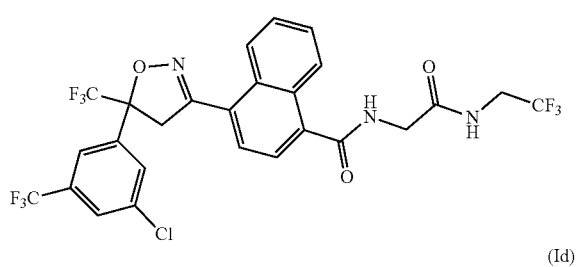

(Ia)

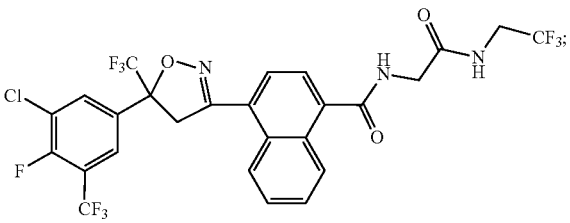

(Id)

ii) a polymer matrix which consists of at least one of polybutylene succinate (PBS), polybutylene succinate adipate (PBSA), ethylene-vinyl acetate copolymer (EVA), and polyvinyl chloride;
  iii) optionally, a plasticizer; and
  iv) optionally, a stabilizer and/or an antioxidant.

25. The antiparasitic external device according to paragraph 24, wherein the polymer matrix consists of ethylene-vinyl acetate copolymer (EVA) with 5 to 95% vinyl acetate, preferably 5-50% vinyl acetate, and most preferably 5-30% vinyl acetate.

26. The antiparasitic external device according to paragraph 24 wherein the polymer matrix consists of polybutylene succinate with triethyl citrate.

27. The antiparasitic external device of any one of paragraphs 1 to 26, wherein the antiparasitic external device further comprises one or more additional active agents.

28. A method for the treatment and/or prevention of a parasitic infestation and/or infection in an animal comprising applying the antiparasitic external device of any one of paragraphs 1 to 27 to an animal in need thereof.

29. Use of an isoxazoline active agent of formula (I), or a pharmaceutically acceptable salt thereof, in the manufacture of an antiparasitic external device.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. An antiparasitic external device for the treatment and/or prevention of a parasitic infection or infestation in an animal comprising:
   i) an effective amount of an isoxazoline active agent of formula (Ia) or (Id):

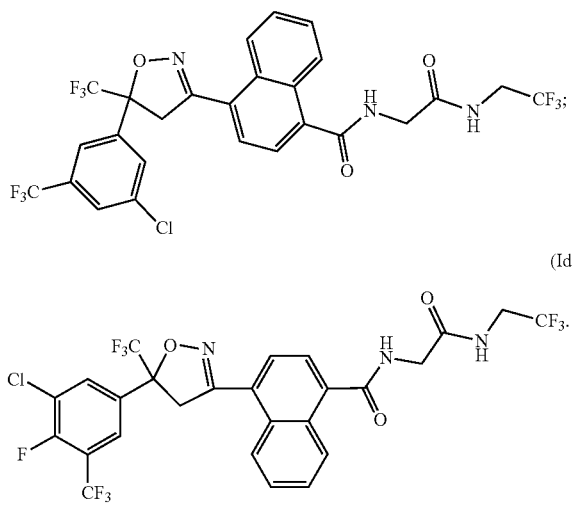

and ii) a polymer matrix comprising ethylene-vinyl acetate copolymer (EVA),
wherein said isoxazoline active agent is dispersed in said polymer matrix.

2. The antiparasitic external device of claim 1, wherein the isoxazoline active agent has the formula (S)-Ia or (S)-Id:

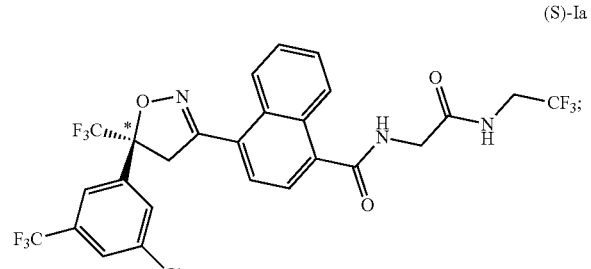

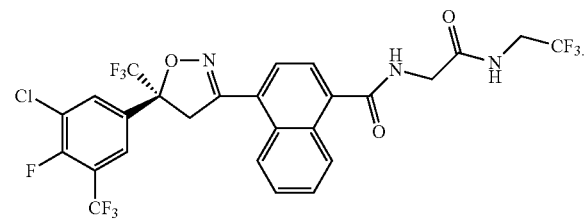

3. The antiparasitic external device of any one of claims 1 and 2, wherein the isoxazoline active agent is present in a concentration of about 1 to about 40% (w/w).

4. The antiparasitic external device of any one of claims 1 and 2, wherein the external device further comprises a plasticizer; optionally, a stabilizer, and optionally, an antioxidant.

5. An antiparasitic external device for the treatment and/or prevention of a parasitic infestation or infection in an animal comprising:
   i) an effective amount of at least one parasiticidal active agent, which is a compound of formula (Ia) or (Id):

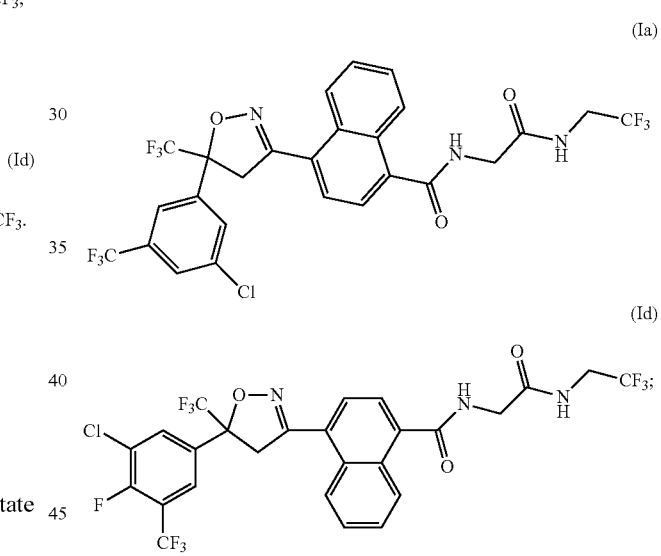

ii) a polymer matrix which consists of ethylene-vinyl acetate copolymer (EVA) with 5-50% vinyl acetate;
   iii) optionally, a plasticizer; and
   iv) optionally, a stabilizer and/or an antioxidant,
wherein said parasiticidal active agent is dispersed in said polymer matrix.

6. The antiparasitic external device according to claim 5, wherein the polymer matrix consists of ethylene-vinyl acetate copolymer (EVA) with 5-30% vinyl acetate, iii) optionally, a plasticizer; and iv) optionally, a stabilizer and/or an antioxidant.

7. The antiparasitic external device of any one of claims 1 and 5, wherein the antiparasitic external device further comprises one or more additional antiparasitic active agents.

8. A method for the treatment of a parasitic infestation and/or parasitic infection in an animal comprising applying the antiparasitic external device of any one of claims 1 and 5 to an animal in need thereof.

* * * * *